United States Patent
Shelchuk

(10) Patent No.: US 7,225,017 B1
(45) Date of Patent: May 29, 2007

(54) PARASYMPATHETIC NERVE STIMULATION FOR ICD AND/OR ATP PATIENTS

(75) Inventor: Anne M. Shelchuk, San Rafael, CA (US)

(73) Assignee: Pacesetter, Inc., Sylmar, CA (US)

( * ) Notice: Subject to any disclaimer, the term of this patent is extended or adjusted under 35 U.S.C. 154(b) by 329 days.

(21) Appl. No.: 10/856,107

(22) Filed: May 28, 2004

Related U.S. Application Data

(63) Continuation of application No. 10/420,998, filed on Apr. 21, 2003.

(60) Provisional application No. 60/388,707, filed on Jun. 12, 2002.

(51) Int. Cl.
*A61N 1/18* (2006.01)

(52) U.S. Cl. .................. 607/4; 607/5; 607/9

(58) Field of Classification Search ........... 607/900, 607/3–5, 9, 14–15, 2
See application file for complete search history.

(56) References Cited

U.S. PATENT DOCUMENTS

| | | | |
|---|---|---|---|
| 4,712,555 A | 12/1987 | Thornander et al. .. | 128/419 PG |
| 4,788,980 A | 12/1988 | Mann et al. ......... | 128/419 PG |
| 4,940,052 A | 7/1990 | Mann et al. ......... | 128/419 PG |
| 4,944,298 A | 7/1990 | Sholder ............... | 128/419 PG |
| 5,199,428 A | 4/1993 | Obel et al. ........... | 128/419 C |
| 5,203,326 A | 4/1993 | Collins ................ | 128/419 PG |
| 5,330,507 A | 7/1994 | Schwartz ............. | 607/14 |
| 5,466,254 A | 11/1995 | Helland .............. | 607/123 |
| 5,476,483 A | 12/1995 | Bornzin et al. ....... | 607/17 |
| 5,522,854 A * | 6/1996 | Ideker et al. ......... | 607/6 |
| 5,578,061 A * | 11/1996 | Stroetmann et al. .... | 607/4 |
| 5,700,282 A | 12/1997 | Zabara ................ | 607/9 |
| 5,836,976 A * | 11/1998 | Min et al. ............ | 607/6 |
| 6,006,134 A * | 12/1999 | Hill et al. ............ | 607/9 |
| 6,134,470 A | 10/2000 | Hartlaub ............. | 607/14 |
| 6,141,590 A * | 10/2000 | Renirie et al. ........ | 607/20 |
| 6,314,323 B1 | 11/2001 | Ekwall ................ | 607/23 |
| 2003/0181951 A1* | 9/2003 | Cates ................. | 607/9 |

FOREIGN PATENT DOCUMENTS

| | | |
|---|---|---|
| EP | 0547734 A2 | 6/1993 |
| EP | 0547734 A3 | 6/1993 |
| EP | 0547734 B1 | 6/1993 |

OTHER PUBLICATIONS

A 1449 filed in parent case, U.S. Appl. No. 10/420,998, filed Apr. 21, 2003 (copies of these not enclosed).
Shamsham, Fadi M.D. et al., "*Essentials of the Diagnosis of Heart Failure,*" American Family Physician (Mar. 1, 2000), vol. 61, No. 5, pp. 1319-1328.
Grassi, Guido M.D. et al., "*Sympathetic Activation and Loss of Reflex Sympathetic Control in Mild Congestive Heart Failure,*" American Heart Association, Inc., CIRCULATION (Dec. 1, 1995), vol. 92, No. 11, pp. 3206-3211.

(Continued)

*Primary Examiner*—Robert Pezzuto
*Assistant Examiner*—Shevon Johnson

(57) ABSTRACT

Exemplary methods for increasing efficiency and/or increasing success of terminating ventricular tachyarrhythmia. An exemplary method includes stimulation of a parasympathetic nerve before, during and/or after delivery of antitachycardia pacing pulses, a cardioversion stimulus and/or a defibrillation stimulus. Various exemplary methods include delivering one or more stimulation pulses during postinspiration. Other methods and/or devices are also disclosed.

3 Claims, 17 Drawing Sheets

OTHER PUBLICATIONS

Eisenhofer, Graeme PhD. et al., "*Cardiac Sympathetic Nerve Function in Congestive Heart Failure*," American Heart Association, Inc., CIRCULATION (May 1, 1996), vol. 93, No. 9, pp. 1667-1676.

Cao, Ji-Min M.D. et al., "*Relationship Between Regional Cardiac Hyperinnervation and Ventricular Arrhythmia*," CIRCULATION (Apr. 25, 2000), pp. 1960-1969.

Cohn, Jay N. M.D., "*Preventing Congestive Heart Failure*," American Family Physician (Apr. 15, 1998), vol. 57, No. 8, pp. 1901-1904.

Frantz, Robert P. M.D., "*Beta Blockade in Patients with Congestive Heart Failure*," Postgraduate Medicine (Sep. 1, 2000), vol. 108, No. 3, pp. 103-118.

Loh, Evan, "*Overview : Old and New Controversies in the Treatment of Advanced Congestive Heart Failure*," Journal of Cardiac Failure, vol. 7, No. 2 (Suppl. 1) (2001).

Gomberg-Maitland, Mardi et al., "*Treatment of Congestive Heart Failure*," American Medical Association, Arch Intern Med. (Feb. 12, 2001), pp. 342-352.

Mendelowitz, David, "*Advances in Parasympathetic Control of Heart Rate and Cardiac Function*," News Physiol. Sci. (Aug. 1999), vol. 14, pp. 155-161.

Pauza, Dainius H. et al., "*Morphology, Distribution, and Variability of the Epicardiac Neural Ganlionated Subplexes in the Human Heart*," The Anatomical Record, 259:353-382 (2000).

Mizeres, Nicholas James, "*The Cardiac Plexus in Man*," The American Journal of Anatomy, vol. 112, No. 2 (Mar. 1963), , pp. 141-155.

Murakami, Masahiko M.D. et al., "*Effects of Cardiac Sympathetic Nerve Stimulation on the Ventricular End-Systolic Pressure-Volume Relationship and Plasma Norepinephrine Dynamics in Dogs*," Japanese Circulation Journal, vol. 61 (Oct. 1997), pp. 864-871.

Du, Xiao-Jun et al., "*Response to Cardiac Sympathetic Activation in Transgenic Mice Overexpressing $B_2$ Adrenergic Receptor*," AM J Physiol Heart Circ Physiol (1996), pp. H630-H636.

Kawada, Toru et al., "*Vagosympathetic Interactions in Ischemia-Induced Myocardial Norepinephrine and Acetylcholine Release*," AM J Physiol Heart Circ Physiol (2001), pp. H216-H221.

Levett, J.M. M.D. et al., "*Cardiace Augmentation Can Be Maintained by Continuous Exposure of Intrinsic Cardiac Neurons to a B-Adrenergic Agonist or Angiotensin II*," Journal of Surgical Research 66, Article 0390, pp. 167-173 (1996).

Burger, Andrew J. M.D. et al., "*Comparison of the Occurrence of Ventricular Arrhythmias in Patients with Acutely Decompensated Congestive Heart Failure Receiving Dobutamine Versus Nesiritide Therapy*," The American Journal of Cardiology, vol. 88 (Jul. 1, 2001), pp. 35-39.

Yuji Murakawa, MD, et al., "Effect of Cervical Vagal Nerve Stimulation on Defibrillation Energy," *Jpn Heart J* (Jan. 2003), vol. 44, pp. 91-100.

* cited by examiner

PARASYMPATHETIC NERVE STIMULATION FOR ICD AND/OR ATP PATIENTS

RELATED APPLICATIONS

This application is a continuation of copending U.S. patent application Ser. No. 10/420,998, filed Apr. 21, 2003, titled "Parasympathetic Nerve Stimulation for ICD and/or ATP Patients", which is a nonprovisional application of Ser. No. 60/388,707, filed Jun. 12, 2002; and is related to copending U.S. patent application Ser. No. 10/460,013, filed Jun. 11, 2003, titled "Vagal Stimulation for Improving Cardiac Function in Heart Failure or CHF Patents".

TECHNICAL FIELD

Exemplary methods and/or devices presented herein generally relate to cardiac pacing and/or stimulation therapy. Various exemplary methods and/or devices concern stimulating parasympathetic nerves in a patient subject to antitachycardia pacing (ATP), cardioversion and/or defibrillation.

BACKGROUND

Implantable cardioverter defibrillators (ICDs) have traditionally been used in patients who survived, or have a high risk of experiencing, a sudden cardiac death event. More recently, indications have been expanded to include patients who have had asymptomatic nonsustained ventricular tachycardia, for example, with decreased ventricular function. Often, an ICD lead is placed in a patient's right ventricle where it provides for sensing of ventricular rate and/or other information for detection of sustained ventricular tachyarrhythmias. Some systems also include an atrial lead, which can, for example, sense atrial activity. Knowledge of both atrial and ventricular information can allow for a comparison of atrial beats in relation to ventricular beats, which, in turn, can help distinguish ventricular tachycardia rhythms from supraventricular tachycardia rhythms. For example, with ventricular tachycardia and complete atrioventricular disassociation, the atrial rate would generally be much lower than the ventricular rate.

Once an ICD device detects a ventricular tachycardia or a ventricular fibrillation, a delay typically occurs wherein the device charges a shock capacitor. The device then discharges the capacitor to deliver a shock, typically of approximately 25 J. An ICD device may also repeat the charge and discharge cycle (e.g., for approximately 5 cycles). Other ICD devices may provide programmable low-energy cardioversion in addition to high-energy shocks. Yet other ICD devices provide a feature that is commonly referred to as "tiered therapy", which typically includes antitachycardia pacing for painless (or relatively painless) termination of monomorphic ventricular tachycardias, programmable low-energy cardioversion, high-energy defibrillation, and backup bradycardia pacing.

A fundamental manner of identifying sustained ventricular tachycardia (VT) involves detecting a heart rate that exceeds a set value, for example, an episode of sustained VT may exhibit a rate in excess of 150 beats per minute (bpm). As already mentioned, other information may be used to distinguish a VT from a supraventricular tachycardia (SVT). Such information can include identification of cycle length stability, abruptness of onset of the tachyarrhythmia, and duration of sustained rate. Regarding ventricular fibrillation (VF), rates in excess of approximately 240 bpm are not uncommon. An ICD, having appropriate defibrillation capabilities can respond to high rates accordingly with defibrillation. Thus, with rates of approximately 150 bpm to approximately 230 bpm, antitachycardia pacing or low-energy may be used; for rates greater than approximately 230 bpm, an ICD device may respond with defibrillation. Of course, the set rates are typically adjustable to account for patient characteristics. Another issue in ICD therapy involves a marked bradycardia following postconversion, which occurs in about 10% of patients successfully converted out of VT or VF. Thus, an ICD device may use backup pacing to prevent and/or minimize postconversion bradycardia.

Regarding antitachycardia pacing, an ICD device may use a technique known as overdrive pacing, which is based on the observation that a mechanism of VT involves re-entry, for example, a circulating wavefront of excitation within a discrete region of myocardium. Often, between the leading edge of the wavefront and the tail of refractoriness, just ahead of the circulating wavefront is a region known as an "excitable gap," which represents a segment of excitable myocardial tissue about to be depolarized by the propagating wavefront. Hence, the excitable gap circulates with the wave of excitation. According to overdrive pacing, an ICD device delivers a train of rapidly paced pulses to increase the probability of invasion of the excitable gap, for example, antitachycardia pacing can use of a burst of ventricular paced pulses (e.g., a burst of approximately 15 individual pulses). Burst pacing can further involve ramp pacing (e.g., decreasing temporal spacing of individual pulses in a burst with respect to time) and/or scanning (e.g., decreasing temporal spacing between bursts). In general, an ICD device uses antitachycardia pacing as a first tier of therapy, for example, in patients with VT and a heart rate less than approximately 180 bpm. Again, if termination does not occur after first-tier therapy, then the ICD device may implement a more aggressive therapy (e.g., low-energy cardioversion).

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of an ECG. Again, defibrillation therapy typically involves high-energy shocks (e.g., 0.1 J to 40 J), which can include monophasic or unidirectional and/or biphasic or bidirectional shock waveforms. Defibrillation may also include delivery of pulses over two current pathways.

Overall, antiarrhythmia therapies, such as antitachycardia pacing, cardioversion and defibrillation therapies, can tax an implantable device's resources; however, treatment of the underlying conditions is often imperative because they may be life-threatening. Thus, a need exists for methods and/or devices that can balance these concerns by conserving device resources and/or treating underlying conditions more effectively. In particular, a need exists for methods and/or devices that can help prevent any immediate reoccurrence of arrhythmia after therapy delivery.

SUMMARY

Exemplary methods for increasing efficiency and/or increasing success of therapies to terminate ventricular tachyarrhythmia, including ventricular fibrillation and ventricular tachycardia. An exemplary method for terminating ventricular tachyarrhythmia includes detecting a ventricular tachyarrhythmia, delivering antitachycardia therapy stimulation, and delivering a stimulation pulse to a lead having one or more electrodes positioned proximate to a parasympathetic pathway. Such an exemplary method optionally includes delivering to a parasympathetic pathway postinspiration only and/or during a refractory period. In general, such exemplary methods cause release of acetylcholine.

Another exemplary method for terminating ventricular tachyarrhythmia includes detecting a ventricular tachyarrhythmia, delivering cardioversion stimulation, and delivering a stimulation pulse to a lead having one or more electrodes positioned proximate to a parasympathetic pathway. Such an exemplary method optionally includes delivering to a parasympathetic pathway postinspiration only and/or during a refractory period. In general, such exemplary methods cause release of acetylcholine.

Yet another exemplary method for terminating ventricular tachyarrhythmia includes detecting a ventricular tachyarrhythmia, delivering defibrillation stimulation, and delivering a stimulation pulse to a lead having one or more electrodes positioned proximate to a parasympathetic pathway. Such an exemplary method optionally includes delivering to a parasympathetic pathway postinspiration only and/or during a refractory period. In general, such exemplary methods cause release of acetylcholine.

Various exemplary devices for performing such exemplary methods are also disclosed herein along with a variety of other exemplary methods and/or devices. In general, the various devices and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary methods disclosed herein rely on parasympathetic stimulation to augment antitachycardia pacing, cardioversion and/or defibrillation therapy. Such methods aim to increase parasympathetic tone typically following delivery of antitachycardia pacing, cardioversion and/or defibrillation therapy. Of course, such methods may aim to increase parasympathetic tone prior to or during administration of antitachycardia pacing, cardioversion and/or defibrillation therapy. Accordingly, the increase in parasympathetic tone decreases probability of arrhythmia reinitiation (i.e., increases probability of successful arrhythmia termination). The increase in probability of success, in turn, can conserve an implantable device's limited resources and thereby increase device longevity. More specifically, antitachycardia pacing, cardioversion and/or defibrillation therapy may occur at a lower energy level or may need to be applied less frequently. In addition, parasympathetic stimulation via delivery of a stimulation pulse may occur according to stimulation pulse parameters wherein the parameters are based at least in part on a probability of reinitiation of an arrhythmia (e.g., ventricular tachyarrhythmia, etc.).

Exemplary Stimulation Device

The techniques described below are intended to be implemented in connection with any stimulation device that is configured or configurable to stimulate nerves and/or stimulate and/or shock a patient's heart.

Figure 1:
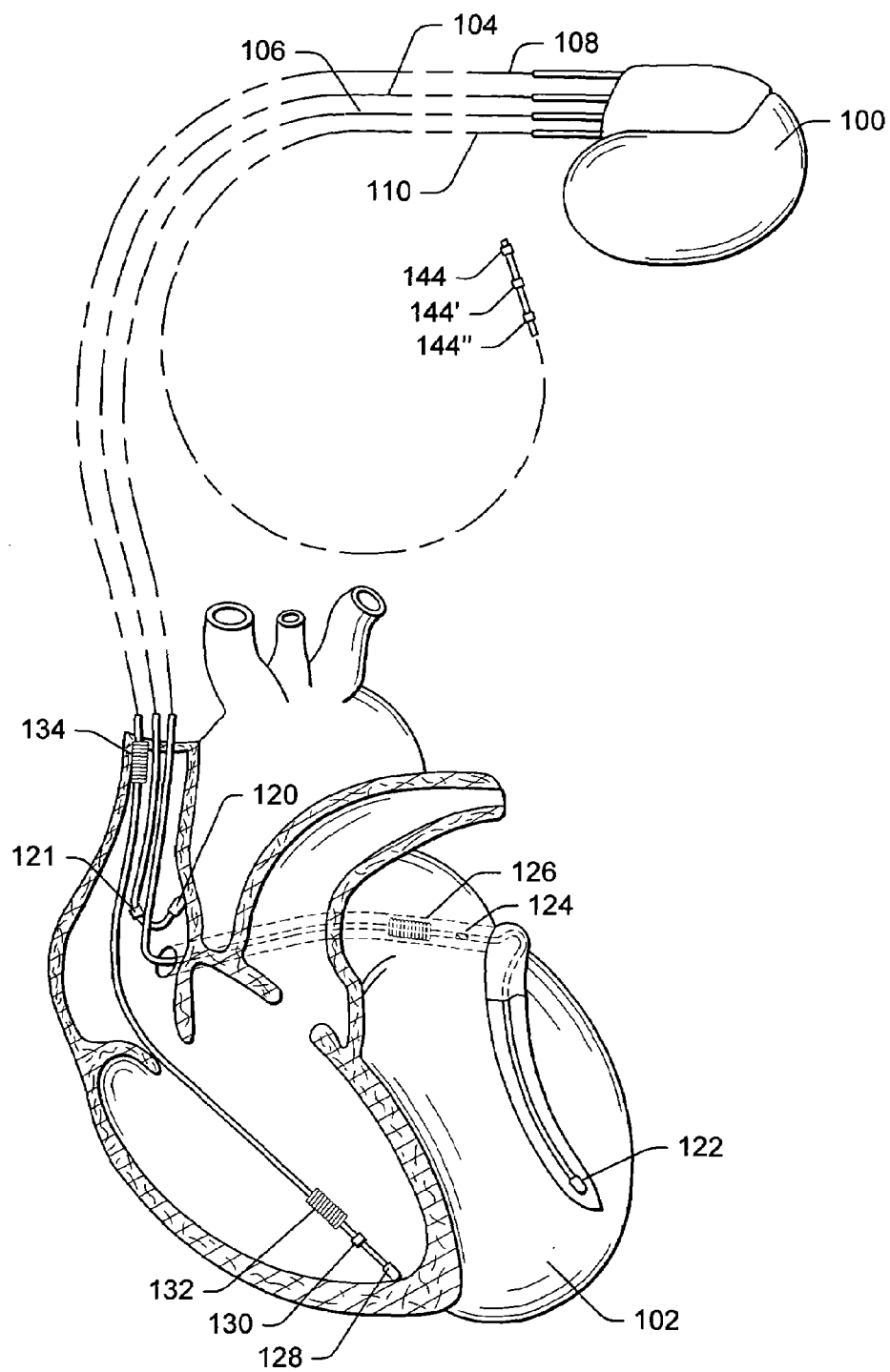
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves and/or afferents nerves that, in turn, stimulate autonomic nerves. In addition, the device 100 includes a fourth lead 110 having, in this implementation, three electrodes 144, 144', 144" suitable for stimulation of autonomic or afferent nerves. This lead may be positioned in and/or near a patient's heart or at or near an autonomic or an afferent nerve, which may be remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic or afferent nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic or afferent nerve stimulation functionality and may further include bifurcations or legs. For example, an exemplary coronary sinus lead includes pacing electrodes capable of delivering pacing pulses to a patient's left ventricle and at least one electrode capable of stimulating an autonomic or an afferent nerve. An exemplary coronary sinus lead (or left ventricular lead or left atrial lead) may also include at least one electrode capable of stimulating an autonomic or an afferent nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic or an afferent nerve, such an electrode may be positioned on the lead or a bifurcation or leg of the lead.

Figure 2:
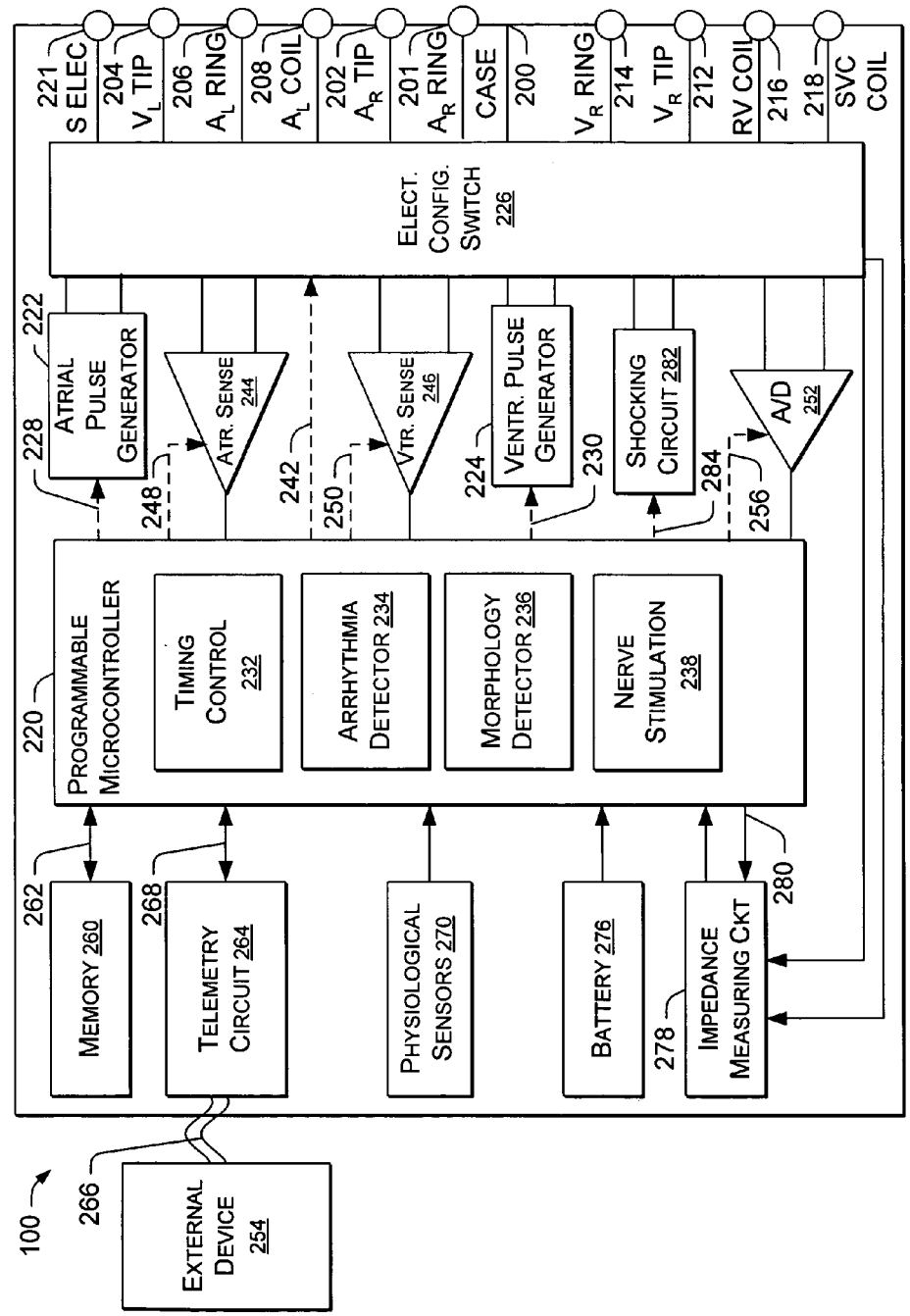
FIG. 2 is a functional block diagram of an exemplary implantable stimulation device illustrating basic elements that are configured to provide cardioversion, defibrillation, pacing stimulation and/or autonomic nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic or afferent nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, and/or afferent nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or nerve stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or nerve stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable nerve stimulation electrodes is also possible via these and/or other terminals (e.g., via a nerve stimulation terminal S ELEC 221).

To support right chamber sensing, pacing, shocking, and/or nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic or afferent nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes a nerve stimulation module 238 for performing a variety of tasks related to nerve stimulation. This component can be utilized by the stimulation device 100 for determining desirable times to administer various therapies, including, but not limited to, parasympathetic stimulation (e.g., direct and/or indirect). The nerve stimulation module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation," to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD)

device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Physiological Heart Conditions Germane to Therapy

A brief overview of various physiological heart conditions follows wherein various deleterious conditions may increase risk of arrhythmia. Some of the conditions involve activation and/or suppression of autonomic pathways. For example, some conditions are associated with an increased sympathetic tone, which may increase risk of reoccurrence of an arrhythmia following administration of a termination therapy. As described further below, various exemplary methods aim to decrease reoccurrence of arrhythmias following antitachycardia pacing, cardioversion and/or defibrillation therapy. In general, such methods call for an increase in parasympathetic tone, which is often in competition with sympathetic tone. Thus, conditions associated with an increased sympathetic tone may act to increase risk of reoccurrence of an arrhythmia following termination therapy. Hence, exemplary methods that call for an increase in parasympathetic tone may be particularly well-suited to treat such conditions. In particular, various exemplary methods can have an effect similar to that achieved by administration of an angiotensin-converting enzyme (ACE) inhibitor, which is commonly administered to congestive heart failure (CHF) patients. A brief discussion of CHF and other conditions associated with arrhythmia follows.

Congestive Heart Failure (CHF)

Congestive heart failure (CHF) is a condition that is often associated with a weakened heart that cannot pump enough blood to body organs. Heart failure may affect either the right side, left side, or both sides of the heart. As pumping action is lost, blood may back up into other areas of the body, including the liver, gastrointestinal tract, and extremities (e.g., right-sided heart failure), or the lungs (e.g., left-sided heart failure). Structural or functional causes of heart failure include high blood pressure (hypertension), valvular heart disease, congenital heart diseases, cardiomyopathy, heart tumor, and other heart diseases. Precipitating factors include infections with high fever or complicated infections, use of negative inotropic drugs (such as beta-blockers and calcium channel blocker), anemia, irregular heartbeats (arrhythmias), hyperthyroidism, and kidney disease.

The New York Heart Association (NYHA) has classified heart condition into four classes: Class I—patients with no limitation of activities; they suffer no symptoms from ordinary activities; Class II—patients with slight, mild limitation of activity; they are comfortable with rest or with mild exertion; Class III—patients with marked limitation of activity; they are comfortable only at rest; and Class IV—patients who should be at complete rest, confined to bed or chair; any physical activity brings on discomfort and symptoms occur at rest. Proper treatment of heart failure often relies on assessment of a patient's classification, see, e.g., Shamsham and Mitchell, "Essentials of the diagnosis of heart failure," *Am. Fam. Phys.*, Mar. 1, 2000 (pp. 1319–1330). For example, Shamsham and Mitchell present an algorithm for diastolic dysfunction and systolic dysfunction that references the NYHA classes.

Lack of Baroreceptor Inhibition

A study by Grassi et al., "Sympathetic activation and loss of reflex sympathetic control in mild congestive heart failure," *Circulation*, 92:3206–3211 (1995), recognized that "severe CHF [e.g., NYHA class III and IV] is characterized by sympathetic activation that probably is due, at least in part, to an impairment of reflex restraint of sympathetic tone". Further, Grassi et al., note that in patients with mild CHF, "baroreceptor inhibitory influence on heart rate and MSNA [postganglionic muscle sympathetic nerve activity] is already markedly impaired". Hence, impaired sympathetic control also affects patients classified as being in NYHA class I and II.

Depletion of Myocardial NE Stores

A study by Eisenhofer et al., "Cardiac sympathetic nerve function in congestive heart failure," *Circulation*, 93:1667–1676 (1996), recognized that "increased availability of norepinephrine (NE) for activation of cardiac adrenoceptors (increased cardiac adrenergic drive) and depletion of myocardial NE stores may contribute to pathophysiology and progression of congestive heart failure". Eisenhofer et al., also noted that "increased NE spillover and desensitization of cardiac beta-adrenoceptors are also consistent with increased availability of NE" and that "depletion of NE stores may contribute to decreased cardiac neuronal release of NE and insufficient support of the failing heart". In conclusion, Eisenhofer et al., stated that "decreased NE store size in the failing heart appears to result from . . . chronically increased NE turnover and reduced efficiency of NE reuptake and storage".

Hyperinnervation and Arrhythmia

A study by Cao et al., "Relationship between regional cardiac hyperinnervation and ventricular Arrhythmia," *Circulation*, 101:1960–1969 (2000), reported that "there is an association between a history of spontaneous ventricular arrhythmia and an increased density of sympathetic nerves in patients with severe heart failure". Cao et al., recognized that ventricular tissue is innervated primarily by sympathetic nerves and by parasympathetic nerves to a much lesser extent; they also recognized that myocardial ischemia can cause damage to nerves and subsequent reinnervation. Thus, sympathetic denervation typically leads to reinnervation and, in particular, to hyperinnervation, which on a regional basis, Cao et al., concluded "may play a significant role in arrhythmogenesis in patients with chronic severe congestive heart failure".

ACE Treatment for CHF Patients

One suggested treatment for CHF involves use of an angiotensin-converting enzyme (ACE) inhibitor, see, e.g., Cohn, "Preventing congestive heart failure," *Am. Fam. Phys., Apr.* 15, 1998 (pp. 1901–1907). A number of potential mechanisms have been suggested to explain the efficacy of ACE inhibitors in preventing congestive heart failure. According to Cohn, the simplest explanation is that ACE inhibitors reduce vascular tone and, by lowering impedance, improve emptying of the left ventricle. Improved left ventricular systolic performance may reduce the risk of symptomatic heart failure.

Cohn also reported that another suggested mechanism involves progressive structural changes that occur in the left ventricular myocardium in patients who develop overt heart failure. In this mechanism, myocardial remodeling is characterized by an enlargement of the chamber and an increase in muscle mass. According to this mechanism, the chamber dilation is associated with a progressive reduction in wall motion, eventually resulting in a globally hypokinetic ventricle. ACE inhibitors have been demonstrated to inhibit remodeling associated with the progressive decline of ejection fraction and overt symptoms of heart failure in both animal and human studies. One disadvantage to ACE inhibitors is that they may result in hyperkalemia (elevated levels of potassium in the blood).

Other disadvantages of ACE treatment were reported in a study by Frantz, "Beta blockade in patients with congestive heart failure," *Postgraduate Medicine*, 108(8):103–118 (2000). Frantz noted that "while ACE inhibitors are now a standard component of CHF therapy . . . they are not enough". In particular, Frantz suggested the use of beta blockers in patients with left ventricular systolic dysfunction and congestive heart failure (in NYHA classes I, II, and III), in essence, "to treat LV dysfunction, not just the CHF symptoms". However, Frantz also noted that "heart rate of less than 60 beats per minute, symptomatic hypotension, excessive fatigue, and progressive signs and symptoms of CHF may all be indicators that the beta blocker dose needs to be reduced and certainly not escalated". Thus, patient monitoring may help achieve a proper beta blocker dosage.

While a variety of other treatments exist for patients with decompensated CHF, see, e.g., Loh, "Overview: Old and new controversies in the treatment of advanced congestive heart failure," *J. Card. Fail.*, 7(2 Suppl. 1): 1–7 (2001); and Gomberg-Maitland et al., "Treatment of congestive heart failure," *Arch. Intern. Med.*, 161: 342–349 (2001), as described below, exemplary nerve stimulation and/or pacing therapies can beneficially augment antitachycardia pacing, cardioversion, and/or defibrillation therapy in patients having CHF and/or other rhythm issues.

Autonomic Nervous System

The autonomic nervous system includes sympathetic and parasympathetic pathways. Both pathways include afferent pathways (e.g., from an organ to central neurons) and efferent pathways (e.g., postganglionic neurons from ganglia to an organ) that relate to functioning of the heart. For example, parasympathetic efferent postganglionic neurons, when stimulated, suppress atrial rate and contractile force, atrio-ventricular nodal conduction, and ventricular contractile force, also known as contractility or inotropy. Sympathetic efferent postganglionic neurons, when stimulated, generally increase heart rate and increase contractility. Note that contractility is associated with the term "inotropy," heart rate is associated with the term "chronotropy" and conduction velocity is associated with the term "dromotropy".

As already mentioned, the stimulation of parasympathetic nerves (which for purposes of this disclosure may include afferent nerves that have parasympathetic effect) can act to decrease heart rate while stimulation of sympathetic nerves can act to increase heart rate. In addition, as noted by Mendelowitz, "Advances in parasympathetic control of heart rate and cardiac function," *News Physiol. Sci.*, 14:155–161 (1999), "when both parasympathetic and sympathetic activity are present, parasympathetic activity generally dominates" and "increases in parasympathetic activity to the heart evoke a bradycardia that is more pronounced when there is a high level of sympathetic firing". Mendeolowitz also noted that "the release of acetylcholine from parasympathetic neurons might act presynaptically to inhibit the release of norepinephrine from sympathetic nerve terminals".

Regarding sympathetic stimulation, norepinephrine is released by sympathetic nerves. After its release, norepinephrine acts on the sinoatrial node (SA node) to increase the rate of diastolic depolarization, and thereby increase heart rate, and acts on the atrioventricular node (AV node) to increase the velocity of conduction and diminish the refractory period during which the AV node is unresponsive to stimuli coming from the atrium.

Contractility (or inotropy) refers to the force or strength of cardiac muscle contractions. Stimulation of sympathetic nerves causes active contractility whereas Frank-Starling mechanism causes passive contractility. Active contractility involves norepinephrine, which increases myocardial calcium permeability (or conductance) and hence actin/myosin crossbridge interactions. Other mechanisms may also accompany the increase in calcium permeability.

In general, an increase in ventricular contractility causes an increase stroke volume, which, in turn, can increase cardiac output. Cardiac output (CO) depends on heart rate (HR) and stroke volume (SV) (e.g., CO equals HR times SV). Changes in ventricular contractility alter the rate of force and pressure development by the ventricle and therefore change the rate of ejection (i.e., ejection velocity). For example, an increase in contractility shifts the Frank-Starling curve, which causes a reduction in end-systolic volume and an increase in stroke volume. The increased stroke volume also causes a reduction in ventricular end-diastolic volume (i.e., preload). The end-systolic pressure-volume relationship (ESPVR) may define an inotropic state of the ventricle.

Changes in contractility also produce significant changes in ejection fraction (EF). Increasing contractility leads to an increase in EF, while decreasing contractility decreases EF. Therefore, EF is often used as a clinical index for evaluating the inotropic state of the heart. In heart failure, for example, an associated decrease in contractility leads to a fall in stroke volume as well as an increase in preload, thereby decreasing EF. The increased preload, if it results in a left ventricular end-diastolic pressure greater than approximately 20 mmHg, can lead to pulmonary congestion and edema. Treatment of a patient in heart failure with an inotropic drug (e.g., beta-adrenoceptor agonist or digoxin) shifts the depressed Frank-Starling curve up and to the left, thereby increasing stroke volume, decreasing preload, and increasing EF.

Changes in inotropic state are particularly important during exercise. Increases in inotropic state helps to maintain stroke volume at high heart rates. Increased heart rate alone decreases stroke volume because of reduced time for diastolic filling (decreased end-diastolic volume). When inotropic state increases at the same time, this decreases end-systolic volume to maintain stroke volume.

Another term used to describe cardiac operation is "cardiac workload," which is sometimes defined as the product of systolic blood pressure and heart rate. In general, an increase in inotropy, chronotropy and/or dromotropy result in an increase in cardiac workload. Further, sympathetic activity is likely to increase cardiac workload whereas parasympathetic activity is likely to decrease cardiac workload.

Figure 3:
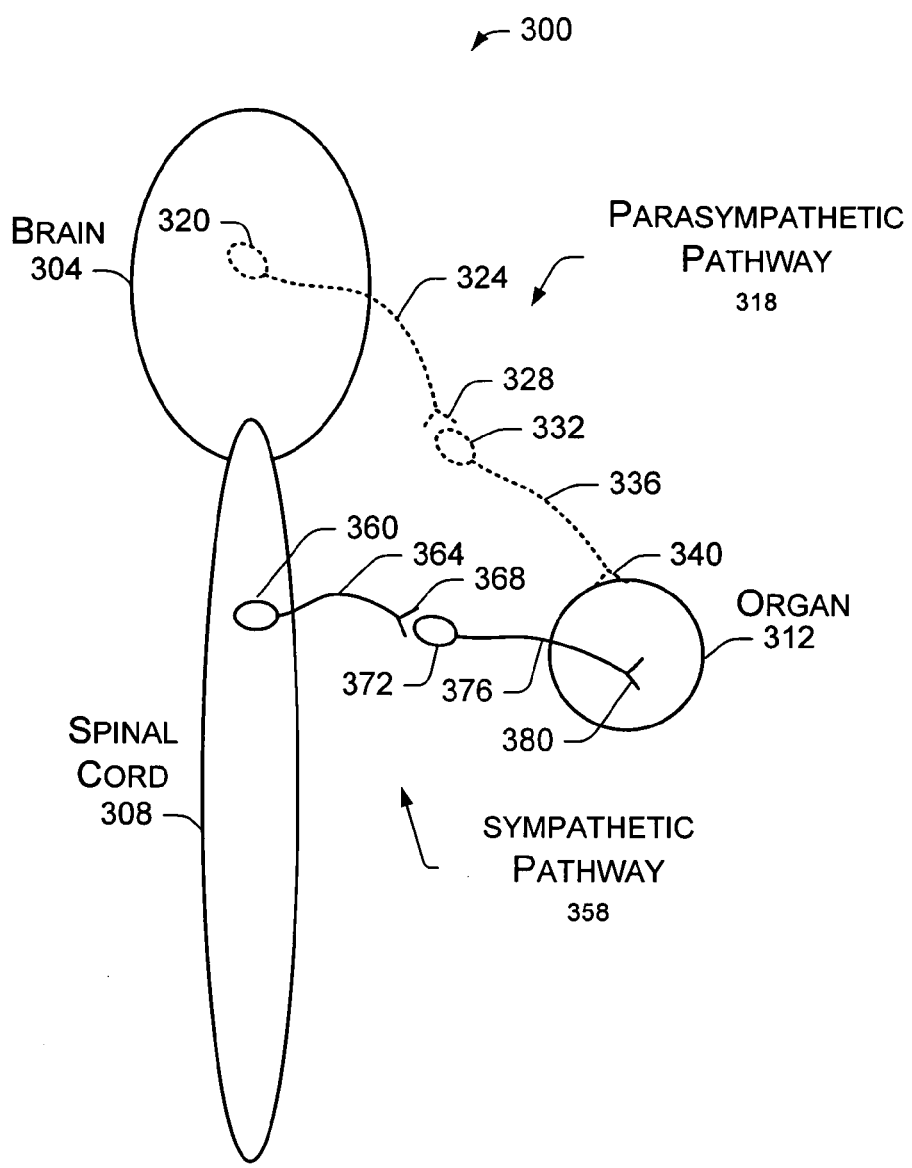
FIG. 3 is a simplified approximate anatomical diagram of a parasympathetic pathway and a sympathetic pathway of the autonomic nervous system.

As already mentioned, the autonomic nervous system includes parasympathetic and sympathetic pathways. Referring to FIG. 3, a simplified diagram of the autonomic nervous system 300 is shown. The system 300 illustrated includes a brain 304, a spinal cord 308, an organ 312, a parasympathetic efferent pathway 318 and a sympathetic efferent pathway 358. The parasympathetic efferent pathway 318 includes a preganglionic cell body 320 located in the brain 304, a preganglionic axon 324, a synaptic cleft 328, a postganglionic cell body 332, a postganglionic axon 336, and a postganglionic synaptic cleft 340 proximate to the organ 312. An exemplary parasympathetic stimulus originates at the brain 304 and ends at the postganglionic synaptic cleft 340 wherein a chemical is emitted to effect cell of the organ 312. A synaptic cleft may also be referred to as a neuroeffector junction. The sympathetic efferent pathway 358 includes a preganglionic cell body 360 located in the spinal cord 308, a preganglionic axon 364, a synaptic cleft 368, a postganglionic cell body 372, a postganglionic axon 376, and a postganglionic synaptic cleft 380 proximate to the organ 312. An exemplary sympathetic stimulus originates at the spinal cord 308 and ends at the postganglionic synaptic cleft 380 wherein a chemical is emitted to effect cell of the organ 312. In both pathways 318, 358, acetylcholine operates as a neurotransmitter to activate postganglionic neurons, i.e., preganglionic neurons are cholinergic. In parasympathetic pathways (e.g., the parasympathetic pathway 318), postganglionic neurons emit acetylcholine and are therefore cholinergic. However, in many sympathetic pathways (e.g., the sympathetic pathway 358), postganglionic neurons emit norepinephrine and are therefore adrenergic. While FIG. 3 shows a one to one ratio of preganglionic to postganglionic neurons, note that a preganglionic neuron generally links to more than one postganglionic neuron, for example, in a sympathetic pathway, a preganglionic neuron to postganglionic neuron ratio may be approximately 1:32. Autonomic pathways than can affect cardiac operation are described in more detail below.

Autonomic Pathways

As already mentioned, the autonomic nervous system includes both sympathetic and parasympathetic nerves. In general, the sympathetic nerves and parasympathetic nerves follow pathways, which, as described in more detail below, are at times to some degree intermingled. Intermingling in the vagosympathetic trunks includes, for example, fibers having a sympathetic core surrounded by a parasympathetic vagal skin. Such "vagosympathetic" fibers may arise from one of the vagosympathetic trunks and descend into epicardial and/or endocardial fibers of the heart. Parasympathetic pathways effecting cardiac operation include the vagus nerve, which is a member of a group of nerves commonly referred to as the cranial nerves. Scientifically, the vagus nerve has been designated as the tenth cranial nerve. There are two of these mixed nerves that act to provide both motor and sensory functions. Each vagus nerve contains both somatic and autonomic branches; however, the autonomic function predominates. Vagus nerves are parasympathetic in nature making up 75% of all parasympathetic fibers passing to the thoracic and abdominal regions of the body. As is the case with most nerves, vagi nerves contain both efferent fibers (e.g., to carry an impulse from its origin in the medulla obligata of the brain to a tissue or an organ), as well as afferent fibers, (e.g., to carry an impulse from a tissue or an organ back to the brain). With vagus nerves, 80% of the fibers are afferent as opposed to efferent. This aids in their active response to the many reflex actions in the body during parasympathetic control. As a whole, the two vagus nerves are very large and work to stimulate a great number of tissues in the body. Vagal stimulation can affect the heart, lungs, esophagus, stomach, small intestine, liver, gall bladder, as well as the upper portions of the ureters.

In general, the right and left vagus nerve pass down the neck as part of right and left vagosympathetic trunks. The right and left vagus also have branches that innervate the heart and lungs. Further down, the left vagus and the right vagus bifurcate into respective left and right ventral and left and right dorsal vagal branches which eventually join. The left and right ventral vagal branches join together to form the ventral vagal trunk on the ventral esophagus while the left and right dorsal vagal branches join together along the dorsal esophagus to form the dorsal vagal trunks. These vagal trunks pass through the esophageal hiatus of the diaphragm and supply the stomach, small intestine, part of the large intestine and major cranial abdominal viscera with parasympathetic innervation. The vagus also includes the right and left recurrent laryngeal nerves, which are somatic, primarily motor subdivisions of the vagus that travel down the neck as part of the right and left vagosympathetic trunks.

Upon stimulation, a vagus nerve releases the hormone acetylcholine at its vagal endings and is, therefore, cholinergic. This is in contrast with adrenergic systems which cause the release of epinephrine and norepinephrine. It is the release of acetylcholine, rather than the passing of nerve impulses that directly initiates a specific response.

Regarding the heart, parasympathetic vagi nerves are distributed to regions of the SA node and the AV node. Release of acetylcholine to these regions typically results in both a decrease in the rate of rhythm of the SA node, as well as a decrease in the cardiac impulse transmission into the ventricles. Consequences of these actions generally include a decrease in heart rate, cardiac output, ventricular contraction, arterial blood pressure, as well as a decrease in overall ventricular pumping.

In general, the right vagus innervates the SA nodal region, the atrial muscle and, to a much lesser degree, the AV nodal region; whereas, the left vagus nerve innervates the SA nodal region and atrial muscle to a lesser degree than it innervates the AV nodal region. Stimulation of the right vagus nerve can predominately slow the SA node rate and thereby reduces heart rate; whereas, stimulation of the left vagus nerve can produce some slowing of the SA node, prolongation of AV conduction and partial or total AV block.

The vagi nerves are also involved in a process known as respiratory sinus arrhythmia (RSA). As stated in Mendelowitz, "Advances in parasympathetic control of heart rate and cardiac function," *News Physiol. Sci.*, 14:155–161 (1999), in RSA, "the heart beats more rapidly in inspiration and slows during postinspiration and expiration". Further, Mendelowitz noted that "cardiac vagal neurons recorded in vivo receive inhibitory synaptic input during inspiration, which is then followed by a rapid depolarization caused by excitatory synaptic input during postinspiration". Various exemplary methods optionally synchronize parasympathetic stimulation with respiratory cycles, for example, by delivering stimuli postinspiration.

Figure 4:
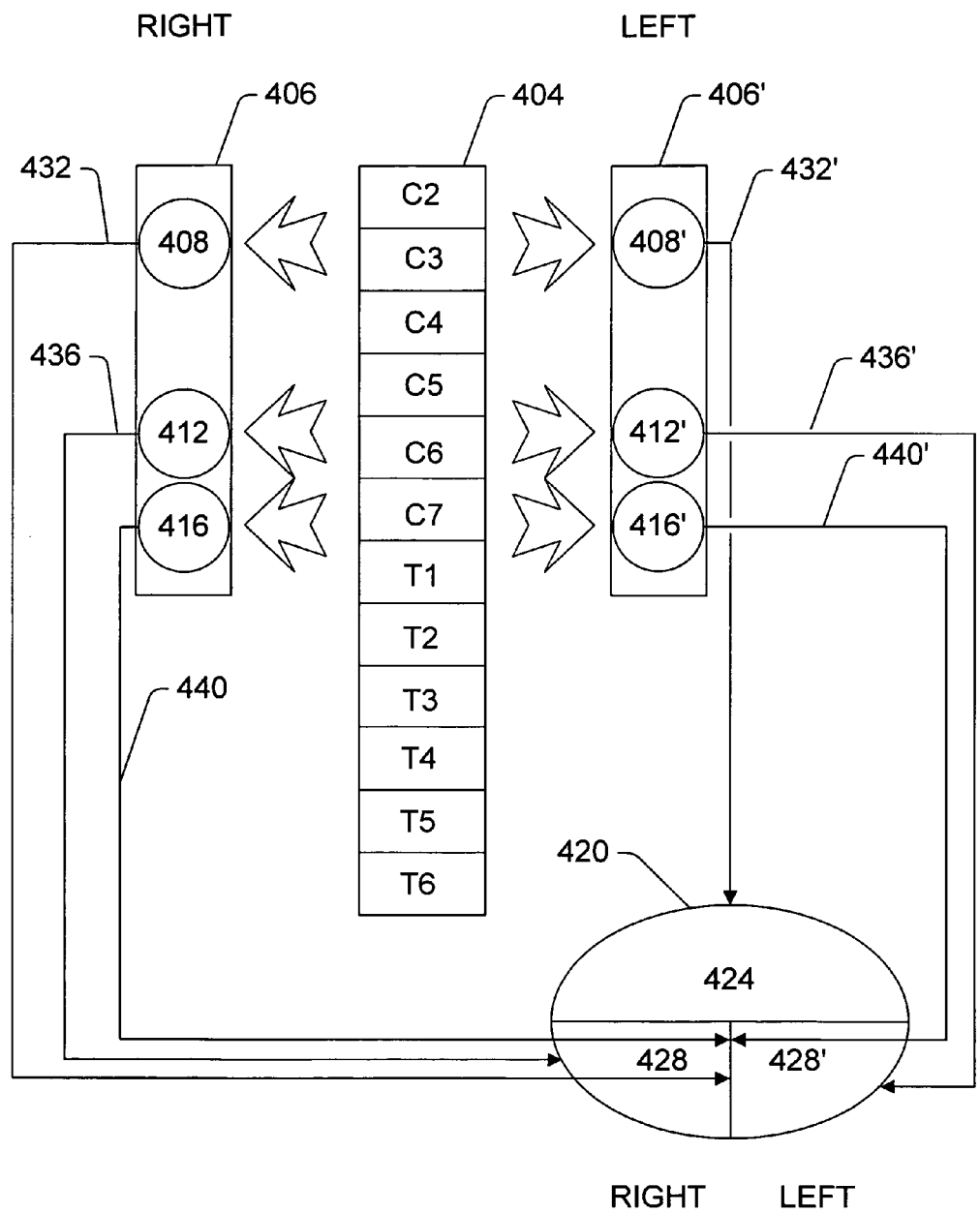
FIG. 4 is a simplified approximate anatomical diagram of sympathetic pathways and/or parasympathetic pathways to the heart.

Referring to FIG. 4, a block diagram of various components of the autonomic nervous system is shown. While FIG. 4 pertains primarily to sympathetic pathways, as already mentioned, intermingling of sympathetic pathways and parasympathetic pathways typically occurs to some degree at various points. The sympathetic nervous system, which is not part of the central nervous system, includes two parallel chains or trunks, a right trunk 406 and a left trunk 406'. Each trunk includes a series of ganglia which lie just lateral to the spinal cord 404 on each side (left and right). In general, the uppermost region of each trunk (406, 406') has three cervical ganglia, which are continuous with the thoracic trunk. The cervical ganglia are known as the right and left superior cervical ganglia (408, 408'), the right and left middle cervical ganglia (412, 412') and the right and left inferior cervical ganglia (416, 416'), the latter of which are known as a stellate ganglion if they combine with a respective first thoracic ganglion. Stellate ganglia exist in approximately 70% to approximately 80% of the population.

Cardiac sympathetic fibers originate in intermediolateral columns of the upper five or six thoracic segments (see T1–T6 in FIG. 4) and lower one or two cervical segments (see C5 and C6 in FIG. 4) of the spinal cord 404. Sympathetic fibers enter the paravertebral chain and typically synapse in the cervical ganglia. Cardiac sympathetic ganglia are generally found close to the spinal column (paravertebral ganglia) and may stem from both thoracic and cervical preganglionic fibers. Postganglionic cardiac sympathetic nerves originate from the left and right ganglia and usually approach the base of the heart (e.g., as superior, middle, and inferior cardiac nerves) along the adventitial surface of the great vessels.

Each of the superior cardiac nerves 432, 432' arises by two or more branches from a respective superior cervical ganglion 408, 408', and occasionally receives a filament from the trunk between a first and/or a second cervical ganglia. The right superior cardiac nerve 432, at the root of the neck, passes either in front of or behind the subclavian artery, and along the innominate artery to the back of the arch of the aorta, where it joins the deep part 428, 428' of the epicardial plexus 420. The right superior cardiac nerve 432 connects with other sympathetic branches. About the middle of the neck the right superior cardiac nerve 432 receives filaments from the external laryngeal nerve; lower down, one or two twigs from the vagus; and as it enters the thorax it is joined by a filament from the recurrent nerve. In addition, filaments from the nerve communicate with the thyroid branches from the right middle cervical ganglion 412. The left superior cardiac nerve 432', in the thorax, runs in front of the left common carotid artery and across the left side of the arch of the aorta, to the superficial part 424 of the epicardial plexus 420.

Each of the middle cardiac nerves 436, 436' (or great cardiac nerves), the largest of the three cardiac nerves, arises from a respective middle cervical ganglion 412, 412', or from a respective trunk 406, 406' between the middle ganglion 412, 412' and the inferior ganglion 416, 416'. On the right side, the right middle cardiac nerve 436 descends behind the common carotid artery, and at the root of the neck runs either in front of or behind the subclavian artery; it then descends on the trachea, receives a few filaments from the recurrent nerve, and joins the right half of the deep part 428 of the epicardial plexus 420. In the neck, it communicates with the right superior cardiac nerve 432 and recurrent nerve. On the left side, the left middle cardiac nerve 436' enters the chest between the left carotid and subclavian arteries, and joins the left half of the deep part 428' of the epicardial plexus 420.

Each inferior cardiac nerve 440, 440' arises from the respective inferior cervical ganglion 416, 416' or the first thoracic ganglion (or stellate ganglion, e.g., 416, 416'). Both right and left inferior cardiac nerves 440, 440' descend behind the subclavian artery and along the front of the trachea, to join the deep part 428, 428' of the epicardial plexus 420. Each of the inferior cardiac nerves 440, 440' communicates freely behind the subclavian artery with the recurrent nerve and the respective middle cardiac nerve 436, 436'.

As already mentioned with reference to FIG. 4, at the base of the heart, the sympathetic fibers form an epicardial plexus 420 that distributes the fibers to the various regions of the heart. The epicardial plexus 420 has a superficial part 424 and a deep part (shown as a right deep part 428 and a left deep part 428' in FIG. 4), see, e.g., *Gray's anatomy: the anatomical basis of medicine and surgery,* 38th ed. (1995). The deep part 428, 428' lies upon the tracheal bifurcation (at the back of the aorta and in front of the tracheal bifurcation) and consists of cardiac branches from all cervical sympathetic ganglia of both right and left sides except the superior left 408', together with superior and inferior cervical and thoracic cardiac branches of the right vagus nerve (parasympathetic) and superior cervical and thoracic branches of the left vagus nerve (parasympathetic).

Figure 5:
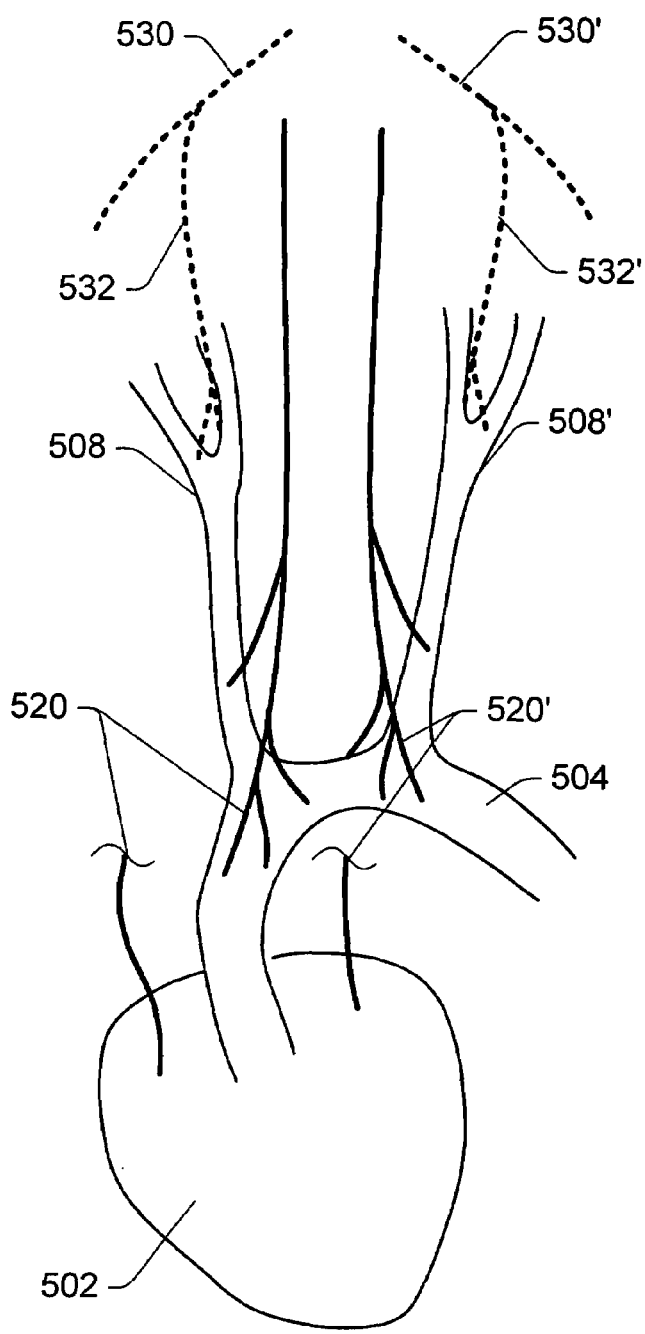
FIG. 5 is a simplified approximate anatomical diagram of parasympathetic afferent pathways.

Referring to FIG. 5, an approximate anatomical diagram of afferent vagal parasympathetic pathways 520, 520' is shown. Vagal afferent pathways include baroreceptors and/or chemoreceptors from the aortic arch 504, carotid arteries 508, 508' and the heart 502. With respect to the heart 502, vagus afferent pathways are known to have receptors associated with atria, ventricles, pulmonary arteries and coronary arteries. Also shown in FIG. 5 are the glossopharyngeal nerves 530, 530' and sinus branches thereof 532, 532'. In general, such afferent pathways lead to the nucleus tractus solitarius in the brainstem. In addition, stimulation of such afferent pathways typically leads to a depressor response. However, a controversial and seemingly undocumented (in humans) reflex known as the "Bainbridge reflex" can increase heart rate due to an increase of the right atrial pressure. In general, cardiac receptors that lead to a neural response are classified as "A" or "B" receptors. B receptors are the predominant stretch receptors and are stimulated by passive stretch of the atria usually during later diastole. B receptors, when stimulated, cause a response similar to baroreceptors, e.g., inhibition of sympathetic nerves and/or excitation of parasympathetic nerves.

Another group of receptors known as left atrial volume receptors respond to increases in transmural pressure: e.g. from increased left atrial volume. Impulses transmitted to the osmoregulatory centers of the hypothalamus result in reduced ADH (antidiuretic hormone, vasopressin) secretion thereby increasing body water loss. Reflex hypotension and bradycardia sometimes follow left atrial distention. With hemorrhage and decreases in left atrial pressure, ADH secretion is increased to induce water retention. Receptors can also cause hormone secretion. For example, mammalian atria have secretory granules containing a small peptide, atrial natriuretic peptide (ANP). ANP is secreted on stretch of the atria. This potent, short lived peptide induces renal secretion of sodium and increase diuresis thus serving to decrease volume. ANP appears to act to decrease CO by decreasing systemic resistance and by increase capillary filtration.

Ventricular, mostly left ventricle, responses include the Bezold-Jarish Reflex, which results from ventricular wall distention stimulating ventricular mechanoreceptors. Such receptors appear to be active only with extreme conditions to protect the ventricle from volume overload (elicit hypotension and bradycardia). The response is a reflex vagal slowing of the heart and simultaneous inhibition of sympathoadrenal activity. The reflex protects against cardiac overstrain, pulmonary edema, and hypovolemia whenever cardiac distention is excessive (e.g., in some CHF patients). The reflex, transmitted by afferent vagal fibers, is thought to exert its sympathetic block via release of endogenous opiods likely acting on the delta-type opiod receptors in the brain.

Epicardial Autonomic Pathways

Pauza et al., "Morphology, distribution, and variability of the epicardiac neural ganglionated subplexuses in the human heart," The Anatomical Record 259(4): 353–382 (2000), reported that the epicardial plexus forms seven subplexuses: (I) left coronary, (II) right coronary, (III) ventral right atrial, (IV) ventral left atrial, (V) left dorsal, (VI) middle dorsal, and (VII) dorsal right atrial. Pauza et al., state that, in general, the human right atrium is innervated by two subplexuses (III, VII), the left atrium by three subplexuses (IV, V, VI), the right ventricle by one subplexus (II), and the left ventricle by three subplexuses (I, V, VI). Pauza et al., also note that diagrams from Mizeres, "The cardiac plexus in man," Am. J. Anat. 112:141–151 (1963), suggest that "left epicardiac subplexuses may be considered as being formed by nerves derived from the left side of the deep extrinsic cardiac plexus, whereas ventral and dorsal right atrial subplexuses should be considered as being supplied by preganglionated nerves extending from the right vagus nerve and right sympathetic trunk, as their branches course in the adventitia of the right pulmonary artery and superior vena cava". Further, Pauza et al., also state that the left coronary (I), right coronary (II), ventral left atrial (IV) and middle dorsal (VI) subplexuses "may be considered as being formed by the deep extrinsic plexus that receives equally from both vagi and sympathetic trunks". Note that in the Pauza et al., reference, the terms "epicardiac preganglionated nerves" and "epicardiac postganglionated nerves" are differentiated from the meanings of "axons of the preganglionic and postganglionic neurons" that are valid in the nomenclature of the autonomic nervous system, for example, as referred to above with reference to FIG. 3 and FIG. 4. Thus, the term "postganglionic neurons" includes epicardiac/epicardial preganglionic neurons as well as epicardiac/epicardial postganglionic neurons.

Neuroeffectors

As already mentioned, upon stimulation, end terminals (or terminal knobs) of the postganglionic sympathetic nerves (e.g., epicardial postganglionic sympathetic nerves) release norepinephrine (NE), which acts upon the myocardium. Following stimulation and release, norepinephrine remains active for several seconds; norepinephrine may then be reabsorbed by the terminal, diffuse out of the area, or be inactivated by enzymes. The adrenal medulla also secretes norepinephrine (e.g., 75 percent epinephrine and 25 percent norepinephrine) and produces a peripheral effect that typically lasts much longer than that produced by stimulation of the sympathetic postganglionic terminal knobs. While circulating norepinephrine can increase contractility, the effect on normally innervated hearts is relatively minor with respect to norepinephrine released by end terminals. Heart rate, although initially stimulated by norepinephrine, usually decreases over time due to activation of baroreceptors and vagal-mediated (parasympathetic) slowing of the heart rate.

Cardiac tissue membrane receptors, such as alpha receptors and beta receptors, receive chemicals emitted by postganglionic nerves. Alpha receptors are the most common type of sympathetic receptor and they respond strongly to norepinephrine and weakly to epinephrine. Beta receptors are also adrenergic and include beta-1, beta-2 and beta-3 receptors. Cardiac sympathetic receptors are mostly the beta-1 subtype. Beta-1 receptors, which respond approximately equally to norepinephrine and epinephrine, generally act on the myocardium to increase heart rate, contractility, and/or conduction velocity. In contrast, parasympathetic cholinergic muscarinic receptors act on the sinoatrial (SA) node to decrease heart rate and act on the atrioventricular (AV) node to decrease conduction velocity. Adrenergic antagonists (indirect action) include beta-blockers such as proranolol and alpha-blockers such as phentolamine that inhibit receptors. Cholinergic antagonists (indirect action) include alpha-blockers such as atropine.

Stimulation of Autonomic Nerves

Nerve stimulation may occur via electrical, magnetic and/or physical stimulation. Electrical stimulation of autonomic nerves has been reported in the literature, see, e.g., Murakami et al., "Effects of cardiac sympathetic nerve stimulation on the left ventricular end-systolic pressure-volume relationship and plasma norepinephrine dynamics in dogs," *Jpn. Circ. J.* 61(10): 864–71 (1997); and Du et al., "Response to cardiac sympathetic activation in transgenic mice overexpressing beta 2-adrenergic receptor". *Am-J-Physiol*. August; 271(2 Pt 2): H630–6 (1996).

According to various exemplary methods and/or devices described herein, a series of pulses, or a pulse train, is typically delivered by an implantable stimulation device to stimulate an autonomic nerve. The pulse train optionally includes pulse parameters or pulse train parameters, such as, but not limited to, frequency, pulse duration (or pulse width), number of pulses, and/or amplitude. These parameters may have broad ranges and vary over time within any given pulse train. In general, a power level for individual pulses and/or pulse trains is determined based on these parameters and/or other parameters. Exemplary ranges for pulse frequency include frequencies ranging from approximately 0.1 to approximately 50 Hz, and, in particular, frequencies ranging from approximately 1 Hz to approximately 20 Hz. Of course, higher frequencies higher than 50 Hz may also be suitable. Exemplary ranges for pulse duration, or pulse width for an individual pulse (generally within a pulse train), include pulse widths ranging from approximately 0.01 milliseconds to approximately 5 milliseconds and, in particular, pulse widths ranging from approximately 0.05 milliseconds to approximately 1.6 milliseconds. Exemplary pulse amplitudes are typically given in terms of current or voltage; however, a pulse or a pulse trains may also be specified by power, charge and/or energy. For example, in terms of current, exemplary ranges for pulse amplitude include amplitudes ranging from approximately 0.02 mA to approximately 20 mA, in particular, ranging from 0.1 mA to approximately 5 mA. Exemplary ranges for pulse amplitude in terms of voltage include voltages ranging from approximately 2 V to approximately 50 V, in particular, ranging from approximately 4 V to approximately 15 V.

For pulses delivered by implantable stimulation devices having a fixed or otherwise limited power supply, i.e., a power supply having power limitations, average power of a pulse or a pulse train is usually limited acutely by the power capability of the power supply (e.g., battery, fuel cell, nuclear generator, etc.) and chronically by the capacity of the power supply and desired longevity of the device's usefulness. Average power of a pulse is generally given as peak power averaged over one cycle. For example, given a voltage of 10 V, a resistance of 1000 ohms, a pulse frequency of 20 Hz and a pulse width of 1 ms, the peak power is given as voltage squared divided by resistance, which is 0.1 W, and the average power is 20 Hz multiplied by 1 ms multiplied by 0.1 W, which is 0.002 W or 2 mW. The term "power", as used herein, includes, but is not limited to, peak power and average power.

Current drain is another factor often considered when determining power limitations of a power supply. Current drain is generally defined as the average amount of current drawn from a power supply in an implantable pulse generator in one hour. Current drain depends on many factors, including how frequently the device delivers pulses and at what parameters, the circuitry and/or the type of stimulation lead. Current drain is commonly expressed in millionths of an ampere or microamperes. A power drain based on current drain may be determined by the product of current drain and voltage. Such a power is optionally useful in determining a maximum power level for an autonomic stimulation pulse or pulses.

In general, a maximum power level or maximum power demand for an implantable device may be determined, in part, by the product of the voltage times the current capability of the battery (or other power supply) less circuit inefficiencies. Of course, desired power supply life (e.g., battery life) and/or other factors may be considered. For example, some implantable stimulation devices have a continuous power drain for one function (e.g., to drive a microchip, microprocessor or timing circuitry) and an intermittent function (e.g., such as pacing, measuring, signaling, etc.) which has intermittent power utilization. Consideration of such factors may be necessary in determining a tolerable and/or maximum power level and, in particular, in determining pulse parameters for autonomic nerve stimulation.

Vessels and Stimulation of Autonomic Pathways

According to various exemplary methods and stimulation devices described herein, and equivalents thereof, stimulation of parasympathetic nerves allows for influence of cardiac activity. For example, various exemplary methods and corresponding stimulation devices rely on placement of one or more electrodes in a vessel, e.g., an epicardial vein or an epicardial venous structure. Suitable epicardial veins or venous structures include the coronary sinus and veins that drain into the coronary sinus, either directly or indirectly. For example, the great cardiac vein passes along the interventricular sulcus, with the anterior interventricular coronary artery, and empties anteriorly into the coronary sinus; and the middle cardiac vein travels with the posterior (right) interventricular coronary artery and empties into the coronary sinus posteriorly. Other suitable veins include those that drain into the right atrium or right auricle. For example, the anterior cardiac vein passes through the wall of the right atrium and empties into the right atrium.

Other exemplary methods and/or devices rely on placement of one or more electrodes in a non-epicardial vein. Such exemplary methods and/or devices are optionally suitable for stimulation of parasympathetic nerves at locations, for example, generally along a parasympathetic pathway between the heart and brain. Further, other exemplary methods and/or devices rely on placing one or more electrodes through the wall of a vein and proximate to a parasympathetic nerve.

Figure 6:
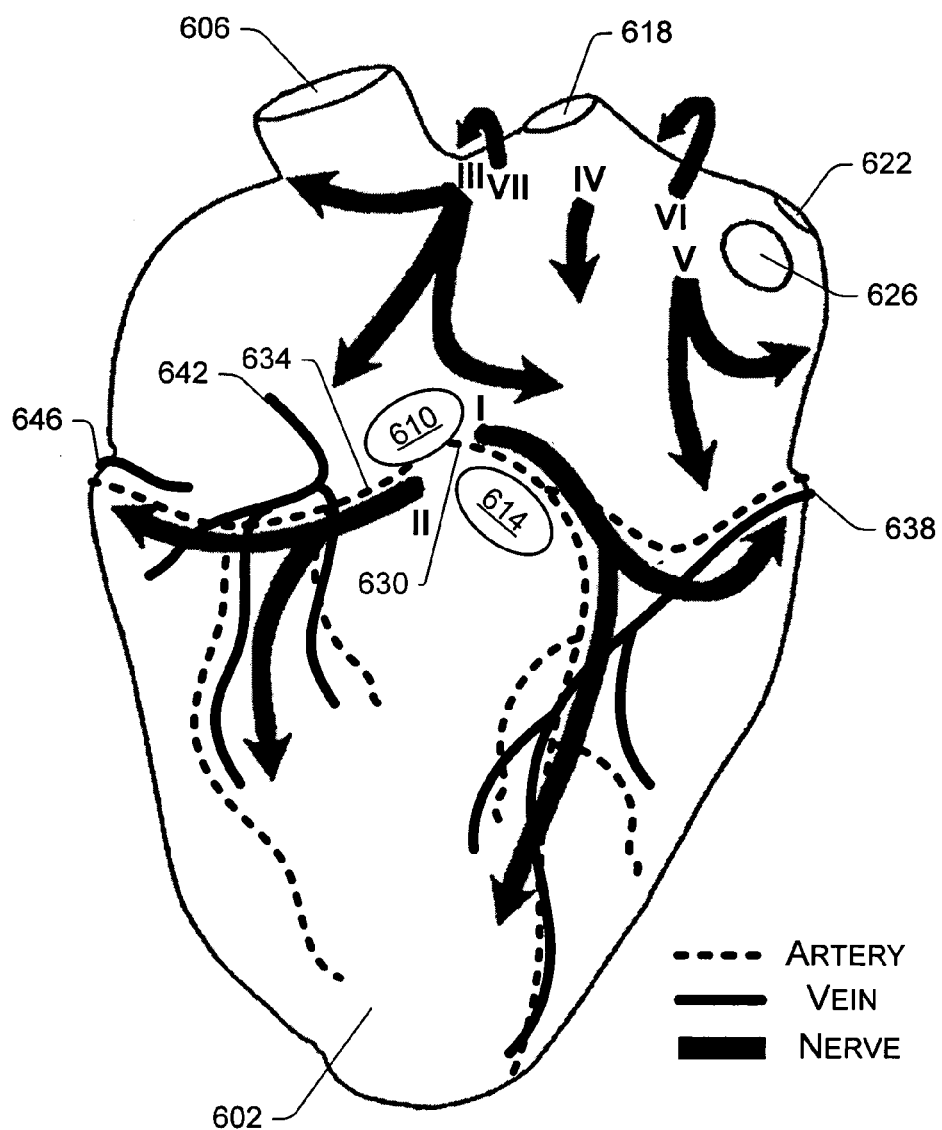
FIG. 6 is an approximate anatomical ventral view diagram of a human heart including some arteries, veins and nerves.

Referring to FIG. 6, a ventral diagram of a human heart 602 is shown. Various anatomical features of the heart 602 are also shown and include an opening to the superior vena cava 606, an opening to the aorta 610, an opening to the pulmonary trunk 614, an opening to the right superior pulmonary vein 618, an opening to the left inferior pulmonary vein 622, and an opening to the left superior pulmonary vein 626. FIG. 6 also shows some of the epicardial arteries (thick dashed lines) and veins (thick solid lines). Under normal conditions, epicardial arteries carry oxygenated blood to the myocardium, primarily myocardium of the ventricles while epicardial veins carry blood deoxygenated by the myocardium to the right atrium of heart 602. Pressure in the veins is generally, on average, much less than pressure in the arteries.

Two major epicardial arterial networks are shown in FIG. 6 and associated with the left coronary artery 630 and the right coronary artery 634. The left coronary artery 630 stems from the aorta near the opening to the aorta 610 and travels along the base of the left ventricle where it branches. One branch of the left coronary artery travels on the epicardial surface of the left ventricle toward the apex of the heart 602 (known as the left anterior descending artery) while another branch travels on the epicardial surface of the left ventricle toward the dorsal side of the heart 602 (known as the circumflex branch of the left coronary artery). The right coronary artery 634 stems from the aorta near the opening to the aorta 610 and travels along the base of the right ventricle where it branches. Various branches of the right coronary artery 634 travel on the epicardial surface of the right ventricle while at least one branch travels on the epicardial surface of the right ventricle toward the dorsal side of the heart 602.

Three major epicardial venous networks are shown in FIG. 6, which are associated with the great cardiac vein 638, the anterior cardiac vein 642, and the small cardiac vein 646. The great cardiac vein 638 receives blood from a network that spreads across the ventral side of the epicardial surface of the left ventricle and major branches of the network extend toward the apex of the heart 602. As already mentioned, the great cardiac vein 638 travels on the epicardial surface near the base of the left ventricle to the dorsal side of the heart 602 where it joins the coronary sinus vein. The anterior cardiac vein 642 receives blood from a network that spreads across the ventral and dorsal sides of the epicardial surface of the right ventricle and major branches of the network extend toward the apex of the heart 602. As already mentioned, the anterior cardiac vein empties into the right atrium of the heart 602. The small cardiac vein 646 travels from the ventral epicardial surface to the dorsal epicardial surface where it empties into the coronary sinus.

FIG. 6 also shows the seven subplexuses as identified by Pauza et al. Preganglionate nerves enter the left coronary subplexus (I) and the right coronary subplexus (II) approximately between the opening to the aorta 610 and the opening to the pulmonary trunk 614. Preganglionate nerves enter the ventral right atrial subplexus (III) at the superior interatrial sulcus and non-regularly on the ventral surface of the root of the superior vena cava while preganglionated nerves enter the ventral left atrial subplexus (IV) approximately between the superior interatrial sulcus and left atrial nerve fold. Preganglionated nerves enter the left dorsal subplexus (V) approximately at the left atrial nerve fold and preganglionated nerves enter the middle dorsal subplexus (VI) approximately between the right and left superior pulmonary veins (see, e.g., 618, 626) and, non-regularly, between the right pulmonary veins and the inferior vena cava. Preganglionated nerves enter the dorsal right atrial subplexus (VII) approximately between the superior vena cava and the right superior pulmonary vein (see, e.g., 606, 618). As already mentioned, postganglionated nerves, and some preganglionated nerves, spread out from the subplexuses (I—VII) across the epicardial surface of the heart 602. The spreading of such nerves is shown by the thick solid arrows in FIG. 6 and FIG. 6, the latter of which shows a dorsal diagram of the heart 602.

Figure 7:
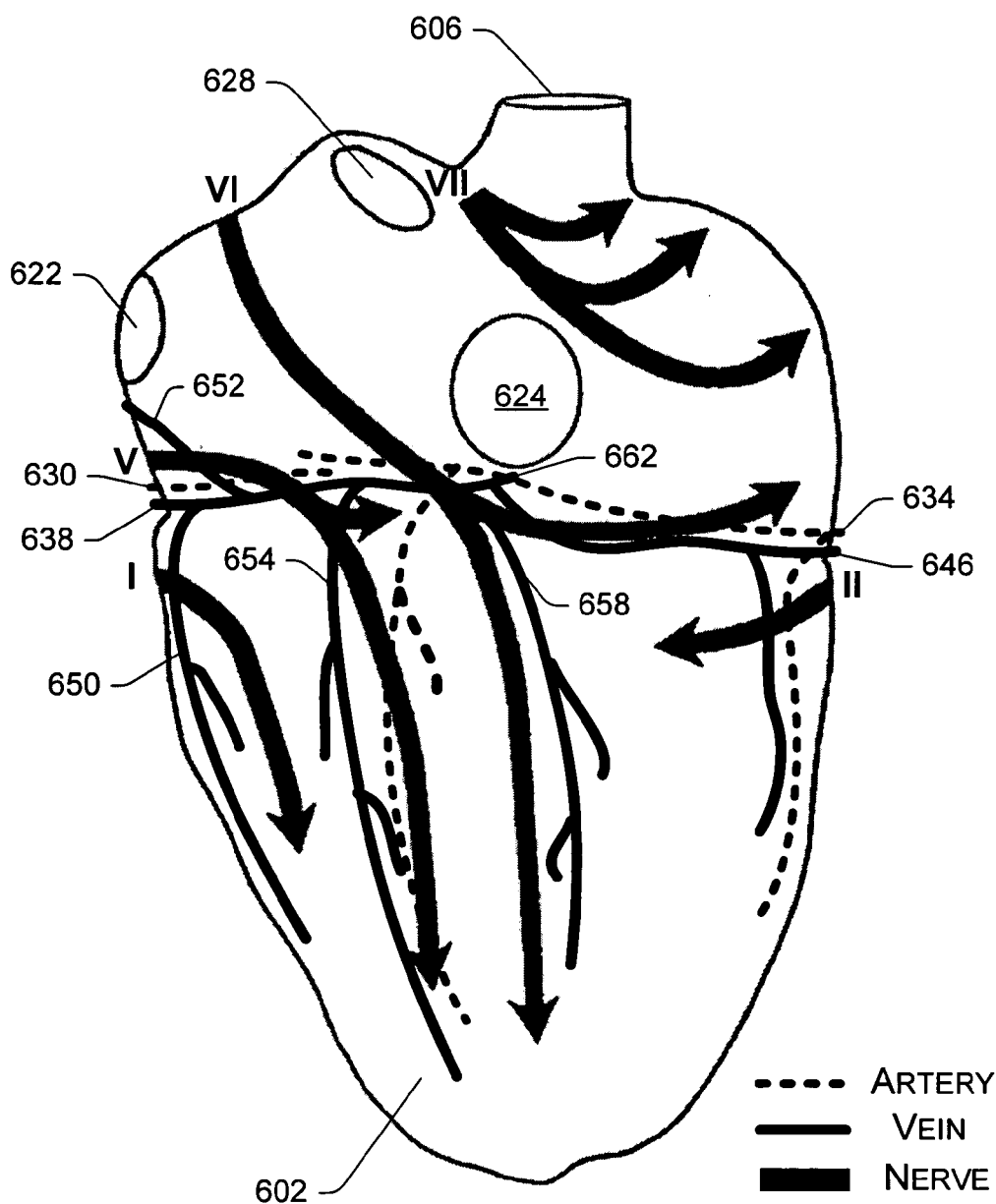
FIG. 7 is an approximate anatomical dorsal view diagram of a human heart including some arteries, veins and nerves.

Referring to FIG. 7, a dorsal diagram of the human heart 602 is shown. Various anatomical features of the heart 602 are also shown and include an opening to the superior vena cava 606, an opening to the inferior vena cava 624, an opening to the right inferior pulmonary vein 628, and an opening to the left inferior pulmonary vein 622. FIG. 7 also shows some of the epicardial arteries (thick dashed lines) and veins (thick solid lines). The arterial and venous networks shown on the dorsal epicardial surface of the heart 602 include extensions of networks from the ventral epicardial surface. For example, the dorsal epicardial surface includes networks stemming the right coronary artery 634 and the left coronary artery 630. In particular, the circumflex branch of the left coronary artery 630 is shown along with various extensions of the right coronary artery 634 one of which approaches the end of the circumflex branch. Venous epicardial structures shown in FIG. 6 include the coronary sinus 662, the great cardiac vein 638, the small cardiac vein 646, the oblique vein of the left atrium 652, the left marginal vein 650, the posterior vein of the left ventricle 654, and the middle cardiac vein 658. The aforementioned veins (638, 646, 650, 652, 654, 658) empty into the coronary sinus 662.

FIG. 7 also shows, via thick solid arrows, neural extensions of five of the subplexuses as identified by Pauza et al. Neural extensions of the left coronary subplexus (I) descend toward the apex of the heart 602 at and/or near the left marginal vein 650 and the posterior vein of the left ventricle 654. Neural extensions of the right coronary subplexus (II) traverse the heart 602 at and/or near the right coronary sulcus. Neural extensions of the left dorsal subplexus (V) descend toward the apex of the heart 602 at and/or near the posterior vein of the left ventricle 654 while neural extensions of the middle dorsal subplexus (VI) descend towards the apex of the heart 602 at and/or near the middle cardiac vein 658 and the small cardiac vein 646. Neural extensions of the dorsal right atrial subplexus (VII) extend around the right atrium at and/or near the superior vena cava (see, e.g., 606) and the inferior vena cava (see, e.g., 624).

As shown in FIGS. 6 and 7, various epicardial veins or venous structures travel at and/or near epicardial subplexuses and/or epicardial extensions of epicardial subplexuses. According to various exemplary methods and/or stimulation devices described herein, at least one electrode is placed in the lumen of an epicardial vein or venous structure and/or through the wall of an epicardial vein or venous structure. Further, upon passing current through the at least one electrode, neural stimulation occurs, which preferably causes release of a neuroeffector, such as, but not limited to, acetylcholine.

Figure 8:
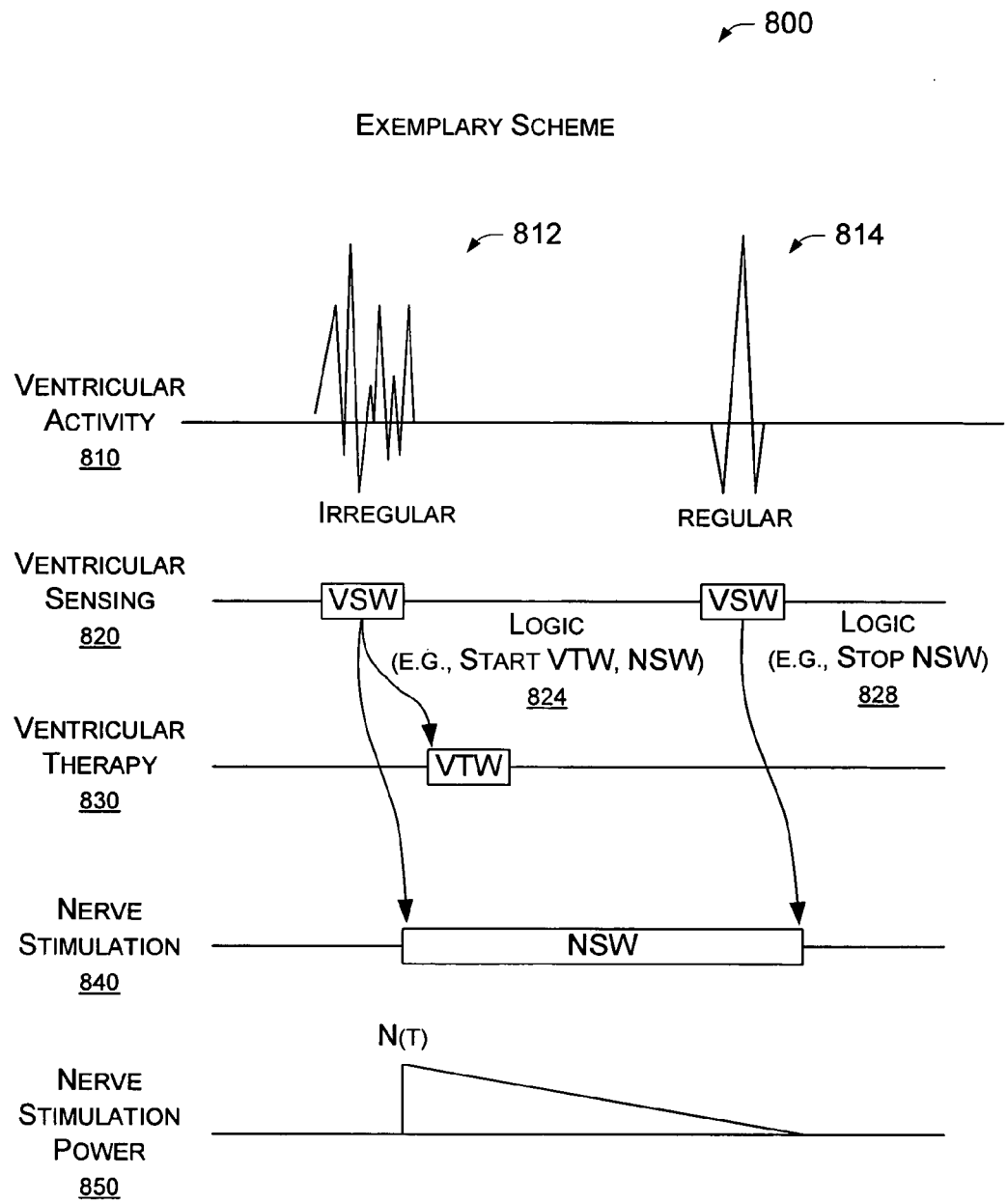
FIG. 8 is an exemplary scheme showing waveforms, logic and associated channels.

FIG. 8 shows an exemplary scheme 800 for nerve stimulation responsive to detection of irregular ventricular activity (e.g., arrhythmia, fibrillation, etc.). A plot 810 of ventricular activity with respect to time includes irregular ventricular activity 812 and regular ventricular activity 814. According to the exemplary scheme 800, ventricular therapy is augmented by nerve stimulation. For example, a ventricular sensing channel 820 includes a sliding ventricular sensing window (VSW). Appropriate logic 824 applied to the events in the sliding window detects the irregular ventricular activity 812 and initiates next steps that include ventricular therapy and nerve stimulation. As shown, a ventricular therapy channel 830 applies ventricular therapy (e.g., antiarrhythmia/fibrillation therapy) within a ventricular therapy delivery window VTW. The ventricular therapy may commence immediately upon detection of the irregular ventricular activity or it may commence after a ventricular therapy delay. As mentioned, the logic 824 also causes, directly or indirectly, a nerve stimulation channel 840 to initiate nerve stimulation (e.g., to increase parasympathetic activity). The nerve stimulation occurs within a nerve stimulation window (NSW) that commences immediately upon detection of the irregular ventricular activity, after delivery of ventricular therapy or after a nerve stimulation delay. The nerve stimulation may continue in the nerve stimulation window (NSW), for example, until regular ventricular activity (e.g., waveform 814) is sensed, or it may expire upon "time out" or it may terminate upon occurrence of an event. Exemplary logic 828 causes the nerve stimulation window (NSW) to terminate upon detection of the regular ventricular activity 814. In addition, nerve stimulation power may vary with respect to time, for example, as shown in the plot 850 of nerve stimulation power versus time (see, e.g., N(t)).

Figure 9:
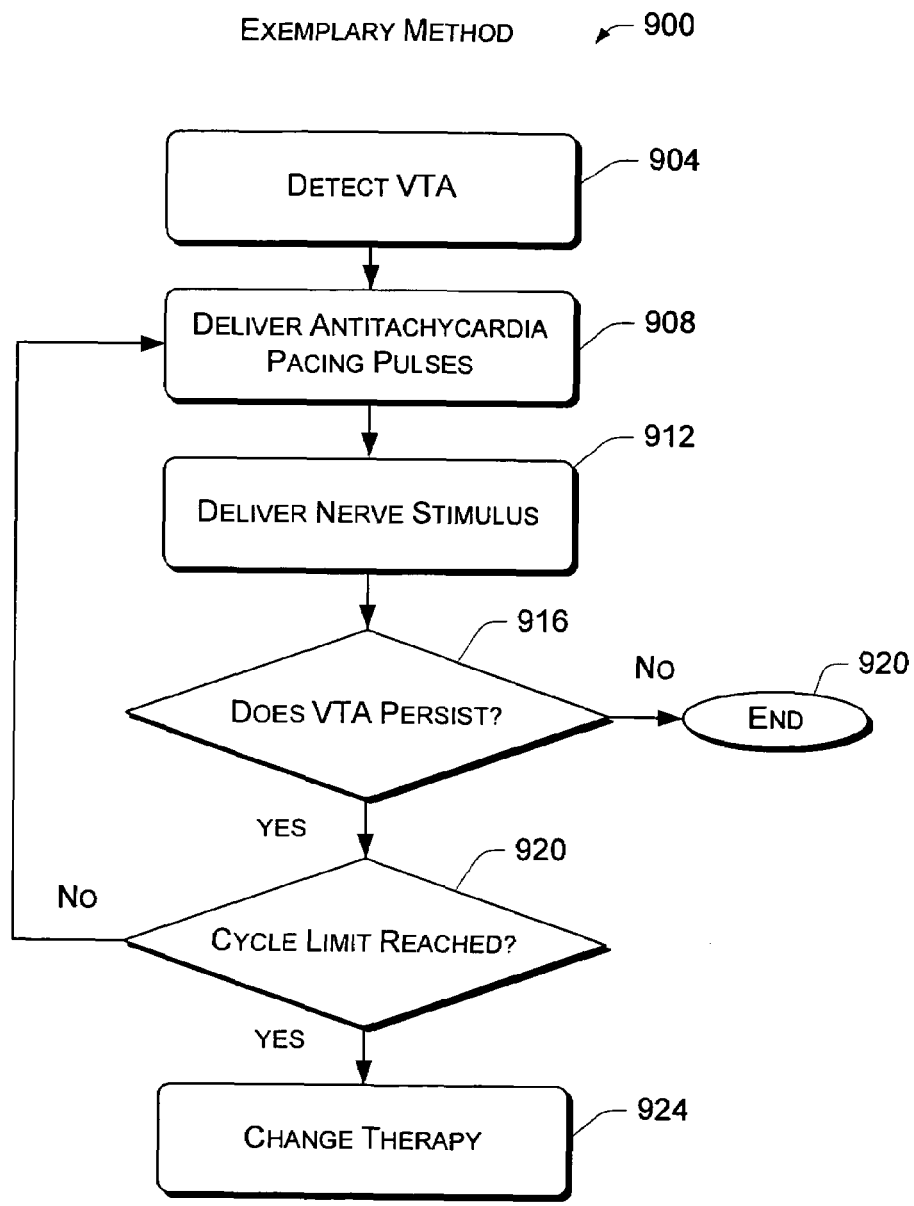
FIG. 9 is a block diagram of an exemplary method for stimulating a parasympathetic nerve and antitachycardia pacing.

Referring to FIG. 9, after an initial positioning of one or more electrodes, proximate to a parasympathetic nerve (e.g., afferent and/or efferent), an exemplary method 900 involves detecting irregular ventricular behavior, administering antitachycardia pacing pulses and delivering a stimulation pulse to the one or more electrodes to thereby stimulate the parasympathetic nerve. More specifically, as shown in FIG. 9, in a detection block 904, a stimulation and/or other device detects a ventricular tachyarrhythmia (VTA), e.g., a VT and/or a VF. Next, in a delivery block 908, a stimulation device delivers antitachycardia pacing pulses (e.g., antitachycardia pacing therapy stimulation). Another delivery block 912 causes a stimulation device to deliver a nerve stimulation pulse to one or more electrodes positioned proximate to a parasympathetic nerve wherein the timing of the nerve stimulation may follow any of the various timings discussed with respect to the exemplary scheme 800 of FIG. 8. Following, or even during nerve stimulation, a determination block 916 determines whether the VTA persists. If the VTA does not persist, then the method 900 terminates in an end block 920. The nerve stimulation may occur according to stimulation pulse parameters (e.g., timing, frequency, pulse width, magnitude, etc.) wherein any of the parameters may be based at least in part on a probability of reinitiation or a probability of termination of an arrhythmia (e.g., ventricular tachyarrhythmia, etc.). The probabilities may be based on past history of successful or unsuccessful termination or other factors.

The nerve stimulation, such as in block 912, may optionally be allowed to continue for a pre-selected duration from stimulation onset. However, if the VTA persists, then the method 900 continues in another determination block 920 that determines whether a cycle limit has been reached. If the cycle limit has not been reached, then the method 900 continues at the delivery block 908 which delivers further ATP therapy. If the cycle limit has been reached, then, in a change therapy block 924, the stimulation device changes the therapy. For example, the exemplary method 900 may continue with a higher tier therapy, such as, but not limited to, cardioversion and/or defibrillation. In addition, at the end block 920 and/or the change therapy block 924, additional parasympathetic stimulation may occur, for example, in a ramp down mode. A ramp down mode may include diminishing energy of parasympathetic stimulation over time, for example, over approximately 20 seconds to approximately 30 seconds. Continued parasympathetic stimulation, in ramp down and/or other modes, can lessen the risk of electrical storm.

Figure 10:
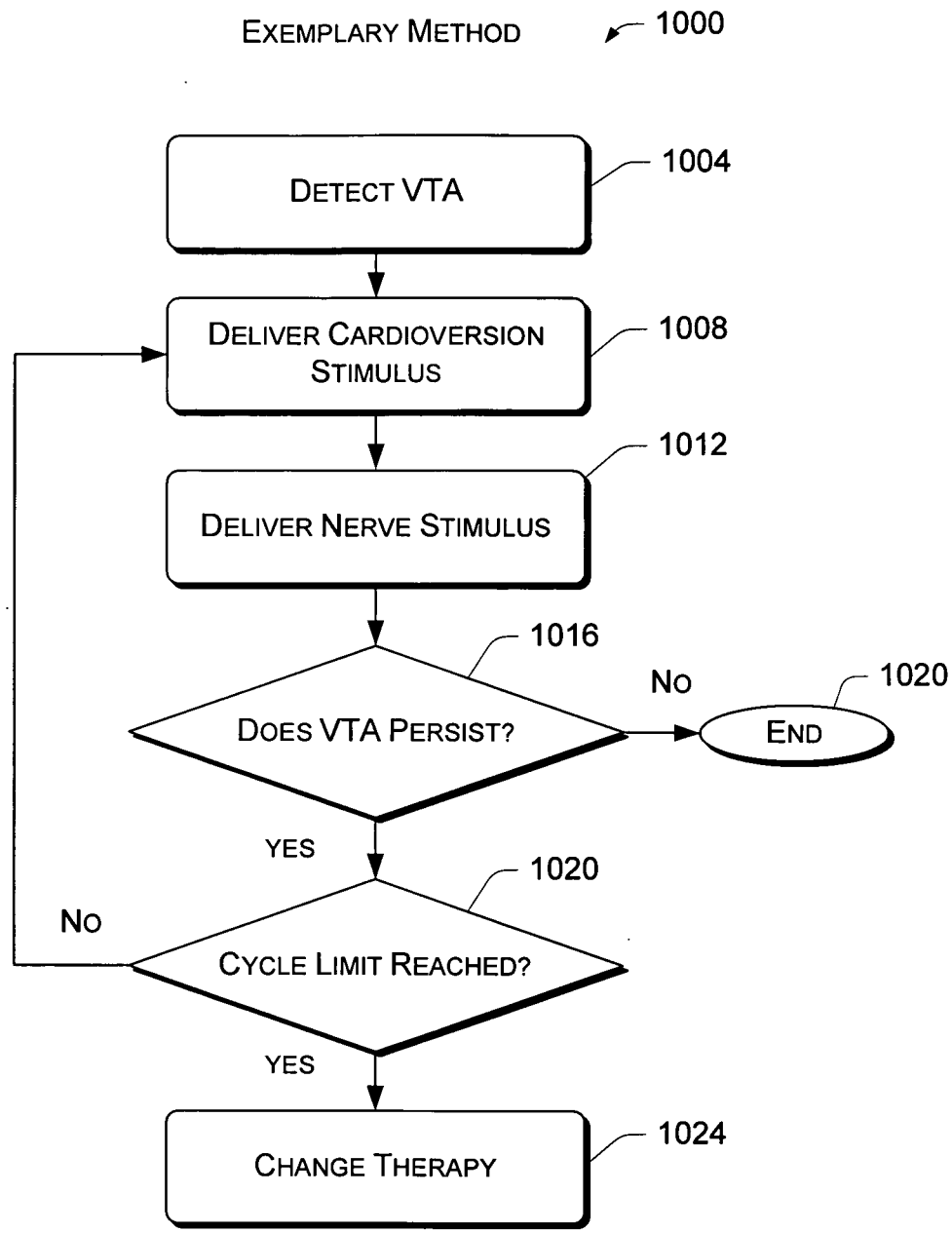
FIG. 10 is a block diagram of an exemplary method for stimulating a parasympathetic nerve and cardioversion therapy.

Referring to FIG. 10, after an initial positioning of one or more electrodes, proximate to a parasympathetic nerve (e.g., afferent and/or efferent), an exemplary method 1000 involves detecting irregular ventricular behavior, administering a cardioversion level stimulus and delivering a stimulation pulse to the one or more electrodes to thereby stimulate the parasympathetic nerve. More specifically, as shown in FIG. 10, in a detection block 1004, a stimulation and/or other device detects a ventricular tachyarrhythmia (VTA), e.g., a VT and/or a VF. Next, in a delivery block 1008, a stimulation device delivers a cardioversion level stimulus (e.g., cardioversion therapy stimulation). Another delivery block 1012 causes a stimulation device to deliver a nerve stimulation pulse to one or more electrodes positioned proximate to a parasympathetic nerve wherein the timing of the nerve stimulation may follow any of the various timings discussed with respect to the exemplary scheme 800 of FIG. 8. Following, or even during nerve stimulation, a determination block 1016 determines whether the VTA persists. If the VTA does not persist, then the method 1000 terminates in an end block 1020. The nerve stimulation may occur according to stimulation pulse parameters (e.g., timing, frequency, pulse width, magnitude, etc.) wherein any of the parameters may be based at least in part on a probability of reinitiation or a probability of termination of an arrhythmia (e.g., ventricular tachyarrhythmia, etc.). The probabilities may be based on past history of successful or unsuccessful termination or other factors.

The nerve stimulation may, such as in block 1012, optionally be allowed to continue for a pre-selected duration from stimulation onset. However, if the VTA persists, then the method 1000 continues in another determination block 1020 that determines whether a cycle limit has been reached. If the cycle limit has not been reached, then the method 1000 continues at the delivery block 1008 which delivers further cardioversion therapy. If the cycle limit has been reached, then, in a change therapy block 1024, the stimulation device changes the therapy. For example, the exemplary method 1000 may continue with a higher tier therapy, such as, but not limited to, defibrillation therapy. In addition, at the end block 1020 and/or the change therapy block 1024, additional parasympathetic stimulation may occur, for example, in a ramp down mode. A ramp down mode may include diminishing energy of parasympathetic stimulation over time, for example, over approximately 20 seconds to approximately 30 seconds. Continued parasympathetic stimulation, in ramp down and/or other modes, can lessen the risk of electrical storm.

Figure 11:
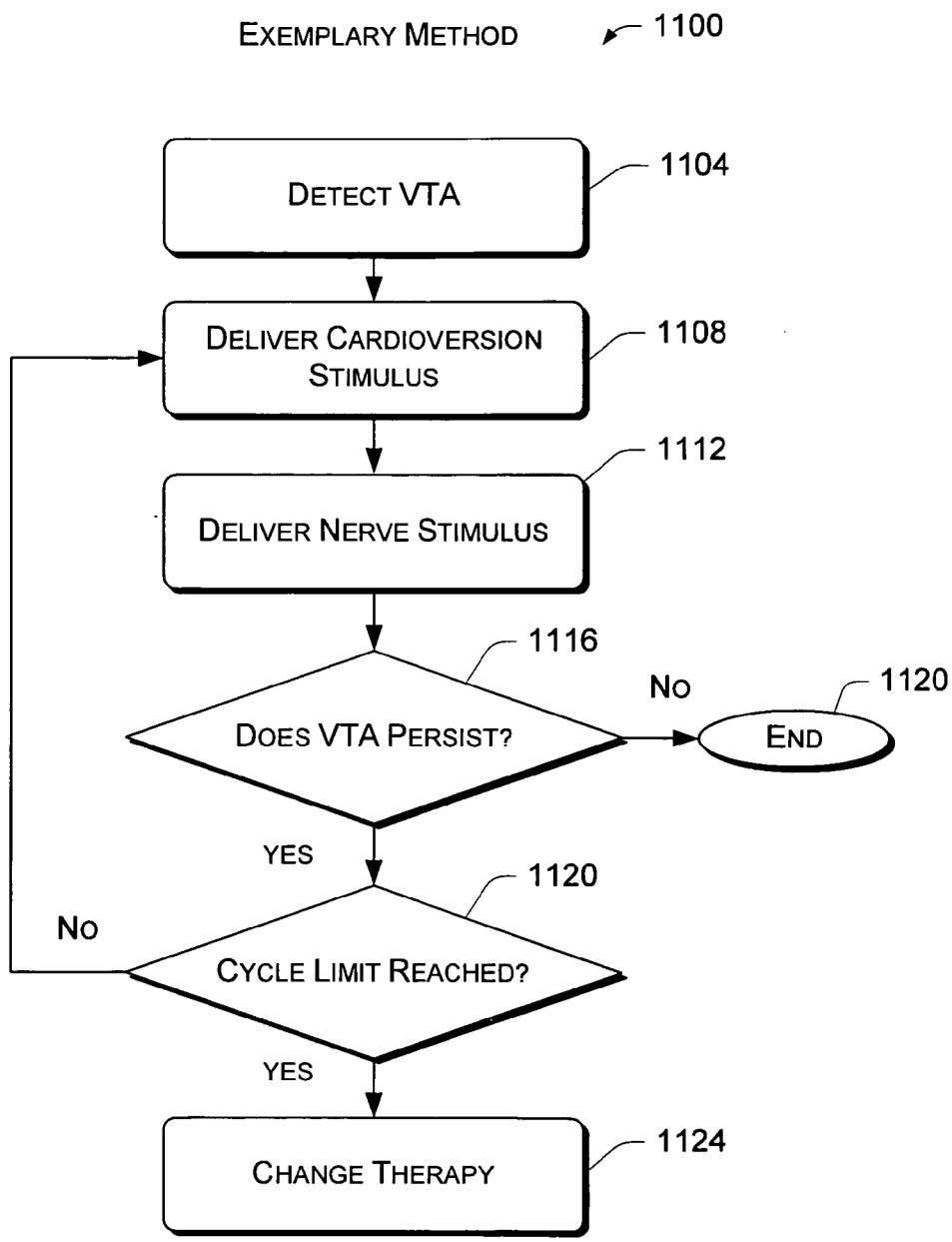
FIG. 11 is a block diagram of an exemplary method for stimulating a parasympathetic nerve and defibrillation therapy.

Referring to FIG. 11, after an initial positioning of one or more electrodes, proximate to a parasympathetic nerve (e.g., afferent and/or efferent), an exemplary method 1100 involves detecting irregular ventricular behavior, administering a defibrillation shock and delivering a stimulation pulse to the one or more electrodes to thereby stimulate the parasympathetic nerve. More specifically, as shown in FIG. 11, in a detection block 1104, a stimulation and/or other device detects a ventricular tachyarrhythmia (VTA), e.g., a VT and/or a VF. Next, in a delivery block 1108, a stimulation device delivers a defibrillation shock (e.g., a defibrillation therapy stimulation). Another delivery block 1112 causes a stimulation device to deliver a nerve stimulation pulse to one or more electrodes positioned proximate to a parasympathetic nerve wherein the timing of the nerve stimulation may follow any of the various timings discussed with respect to the exemplary scheme 800 of FIG. 8. Following, or even during nerve stimulation, a determination block 1116 determines whether the VTA persists. If the VTA does not persist, then the method 1100 terminates in an end block 1120. The nerve stimulation may occur according to stimulation pulse parameters (e.g., timing, frequency, pulse width, magnitude, etc.) wherein any of the parameters may be based at least in part on a probability of reinitiation or a probability of termination of an arrhythmia (e.g., ventricular tachyarrhythmia, etc.). The probabilities may be based on past history of successful or unsuccessful termination or other factors.

The nerve stimulation, such as in block 1112, may optionally be allowed to continue for a pre-selected duration from stimulation onset. However, if the VTA persists, then the method 1100 continues in another determination block 1120 that determines whether a cycle limit has been reached. If the cycle limit has not been reached, then the method 1100 continues at the delivery block 1008 which delivers further defibrillation therapy. If the cycle limit has been reached, then, in a change therapy block 1124, the stimulation device changes the therapy, as appropriate. In addition, at the end block 1120 and/or the change therapy block 1124, additional parasympathetic stimulation may occur, for example, in a ramp down mode. A ramp down mode may include diminishing energy of parasympathetic stimulation over time, for example, over approximately 20 seconds to approximately 30 seconds. Continued parasympathetic stimulation, in ramp down and/or other modes, can lessen the risk of electrical storm.

According to various exemplary methods and/or devices, parasympathetic stimulation occurs optionally at a non-epicardial location and/or at an epicardial location. For example, suitable non-epicardial locations include, but are not limited to, right and left cervical vagal locations. Of course, locations also optionally include those associated with afferent parasympathetic pathways.

Stimulation of Non-Epicardial Parasympathetic Pathways

A study by Kawada et al., *Am. J. Physiol. Heart Circ. Physiol.*, 280:H216–H221 (2001), noted that "the present results imply that the antifibrillatory effect of electrical vagal stimulation is a direct effect of ACh [acetylcholine] on the myocardium rather than the presynaptic inhibition of NE release by ACh". Therefore, according to various exemplary methods described herein, an implantable device delivers one or more stimulation pulses to one or more electrodes located proximate to a parasympathetic pathway. Such an exemplary method aims to stimulate a parasympathetic nerve (e.g., a vagal nerve) and cause release of acetylcholine to thereby produce an antifibrillatory and/or antiarrhythmic effect that can decrease probability of reoccurrence of an arrhythmia.

Stimulation of Epicardial Parasympathetic Pathways

Figure 12:
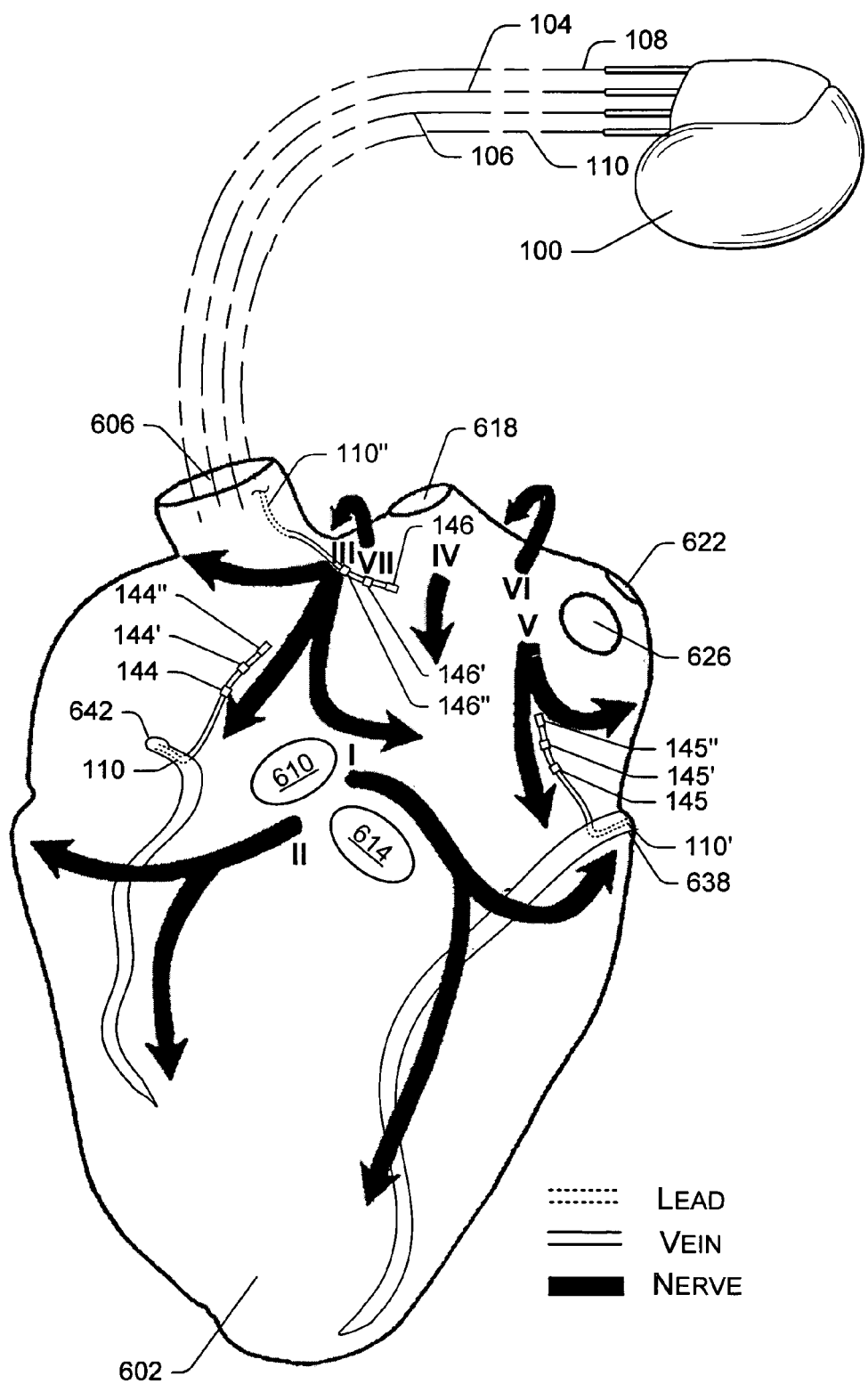
FIG. 12 is an approximate anatomical ventral view diagram of a human heart including some arteries, veins and nerves and stimulation leads associated with a pacing device.

Referring again to FIGS. 6 and 7, various epicardial vessels are shown along with various subplexuses. Referring to FIG. 12, an approximate anatomical diagram of a ventral view of a heart that corresponds to the diagram of FIG. 6 is shown. In FIG. 12, exemplary leads having exemplary electrodes are also shown in exemplary epicardial locations. For example, FIG. 12 shows the exemplary stimulation device 100 of FIG. 1 having four leads 104, 106, 108, 110. The leads 104, 106, 108, 110 optionally include branches or bifurcations. In this example, any of the leads may carry electrodes suitable for stimulation of autonomic nerves. As shown in FIG. 11, one exemplary lead 110 has an electrode portion having three electrodes 144, 144', 144". The electrode portion of the lead 110 passes through the wall of the anterior cardiac vein 642 and extends along nerves emanating from the VRA (III) subplexus. Having an electrode portion of a lead positioned as such, activation of at least one of the electrodes 144, 144', 144" optionally stimulate nerves to release acetylcholine and/or affect operation of the SA node. In a similar manner, another exemplary lead 110' has an electrode portion having three electrodes 145, 145', 145". The electrode portion of the lead 110' passes through the wall of the great cardiac vein 638 and extends along nerves emanating from the LD (V) subplexus. Having an electrode portion of a lead positioned as such, activation of at least one of the electrodes 145, 145', 145" optionally stimulate nerves to release acetylcholine and/or affect operation of the AV node. Yet another exemplary lead 110" has an electrode portion having three electrodes 146, 146', 146". The electrode portion of the lead 110" passes through the wall of the superior vena cava (see, e.g., opening of superior vena cava labeled 606) and extends to the VRA (III) subplexus and/or DRA (VII) subplexus. Having an electrode portion of a lead positioned as such, activation of at least one of the electrodes 146, 146', 146" optionally stimulate nerves to release acetylcholine and/or affect operation of the SA node. Of course, the locations and functions of the three leads 110, 110', 110" are only exemplary as a variety of other arrangements are possible. In general, leads may extend to pre-ganglionated field regions, ganglionated field regions and/or post-ganglionated field regions. More specifically, leads optionally extend to pre-ganglionated field regions, ganglionated field regions and/or post-ganglionated field regions associated with at least one of the seven subplexus identified in the Pauza et al. reference. While the leads shown in FIG. 12 include electrode portions that extend through a vessel and/or chamber wall, other exemplary leads include electrode portions that remain within the lumen of a vessel and/or within a chamber of the heart. Again, such leads optionally extend to pre-ganglionated field regions, ganglionated field regions and/or post-ganglionated field regions associated with at least one of the seven subplexus identified in the Pauza et al. reference. Further, exemplary leads optionally include electrode portions that remain within the lumen of a vessel and/or within a chamber of the heart.

Figure 13:
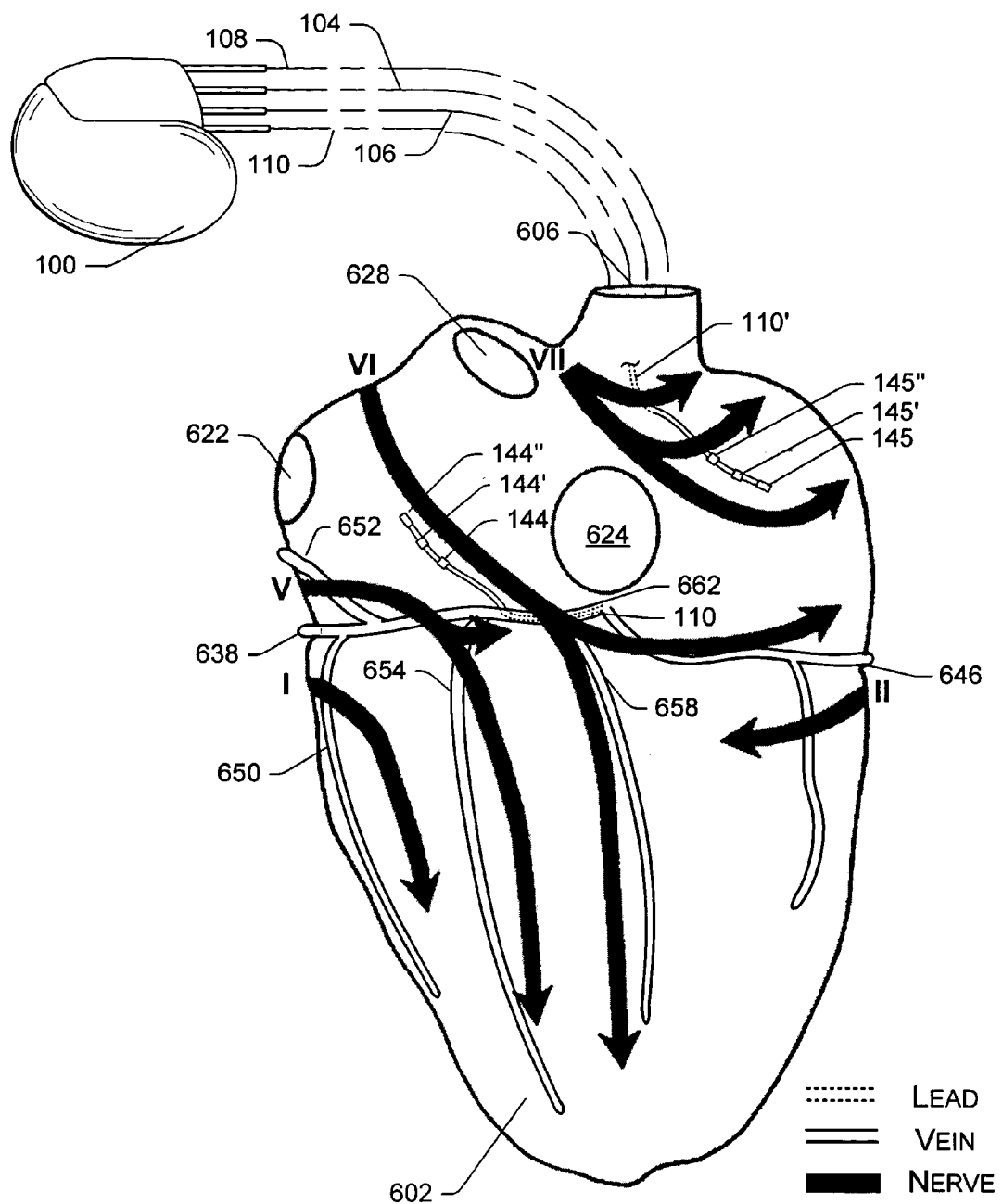
FIG. 13 is an approximate anatomical dorsal view diagram of a human heart including some arteries, veins and nerves and stimulation leads associated with a pacing device.

Referring to FIG. 13, an approximate anatomical diagram of a ventral view of a heart that corresponds to the diagram of FIG. 7 is shown. FIG. 13 shows the exemplary stimulation device 100 of FIG. 1 having four leads 104, 106, 108, 110. The leads 104, 106, 108, 110 optionally include branches or bifurcations. In this example, any of the leads may carry electrodes suitable for stimulation of autonomic nerves. As shown in FIG. 13, one exemplary lead 110 has an electrode portion having three electrodes 144, 144', 144". The electrode portion of the lead 110 passes through the wall of the coronary sinus 662 and extends along nerves emanating from the MD (VI) subplexus and/or LD (V) subplexus. Having an electrode portion of a lead positioned as such, activation of at least one of the electrodes 144, 144', 144" may stimulate nerves to release acetylcholine and/or affect operation of the AV node. In a similar manner, another exemplary lead 110' has an electrode portion having three electrodes 145, 145', 145". The electrode portion of the lead 110' passes through the wall of the superior vena cava (see, e.g., opening of superior vena cava labeled 606) and extends to the DRA (VII) subplexus and/or to nerves emanating from the DRA (VII) subplexus. Having an electrode portion of a lead positioned as such, activation of at least one of the electrodes 145, 145', 145" may stimulate nerves to release acetylcholine and/or affect operation of the SA node. Of course, the locations and functions of the two leads 110, 110' are only exemplary as a variety of other arrangements are possible. In general, leads may extend to pre-ganglionated field regions, ganglionated field regions and/or post-ganglionated field regions. More specifically, leads optionally extend to pre-ganglionated field regions, ganglionated field regions and/or post-ganglionated field regions associated with at least one of the seven subplexus identified in the Pauza et al. reference.

Figure 14:
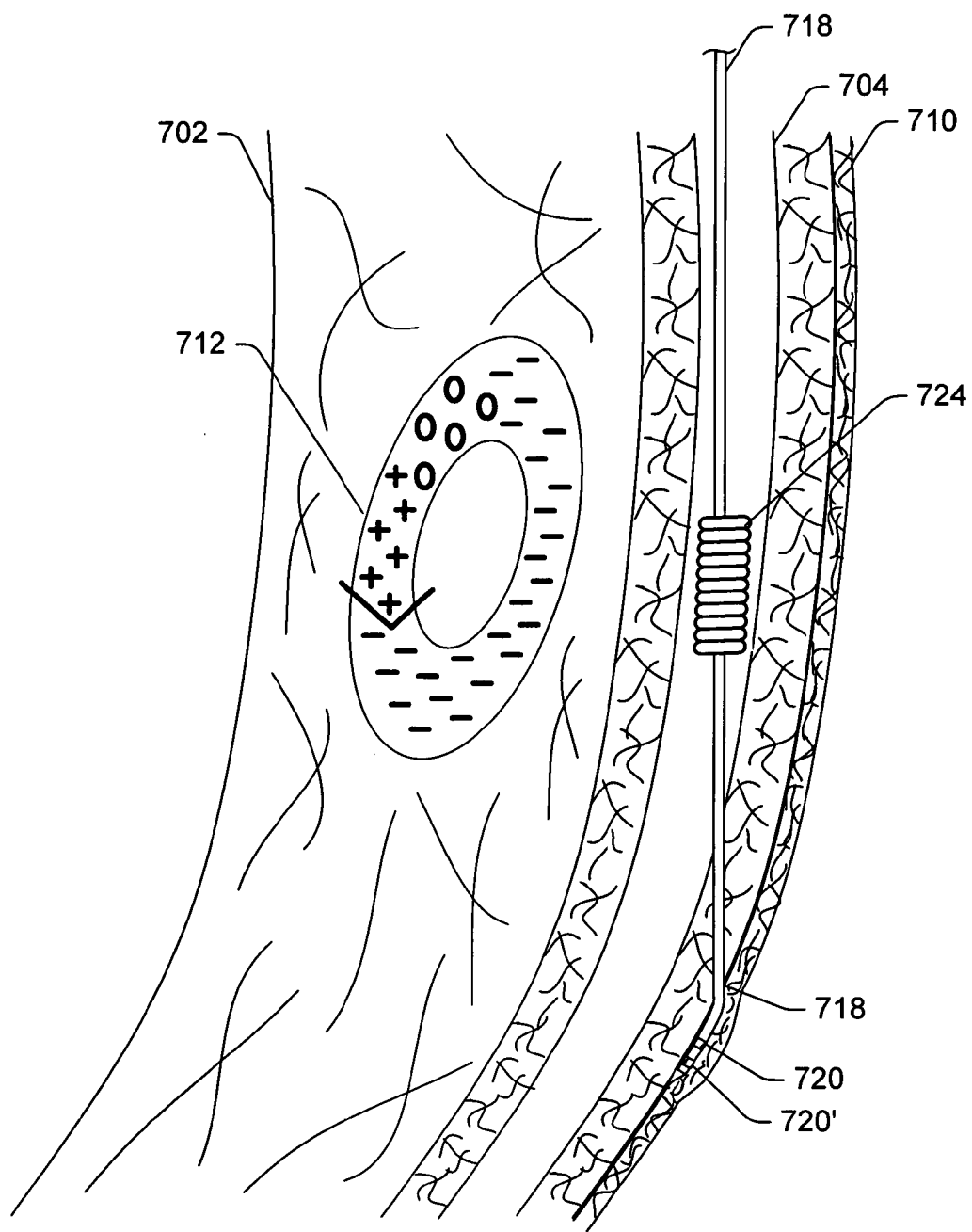
FIG. 14 is an approximate anatomical diagram of a cross-section of a human heart, a re-entrant pathway and a stimulation lead.

Referring to FIG. 14, a simplified approximate anatomical diagram of a cross-section of a heart is shown. From left to right, the diagram includes a cross-section through a heart wall 702, a cross-section through a vein 704 and a cross-section through the pericardium 710. A lead 718 having a large electrode 724 and two smaller distal electrodes 720, 720' are also shown. Note that the distal electrodes 720, 720' are positioned exteriorly of the vein 704, between the vein wall 704 and the pericardium 710.

Also shown in FIG. 14, within the heart wall 702 is a re-entrant pathway or circuit 712. As shown, the re-entrant pathway 712 surrounds a core, which is typically inactive scar tissue. The re-entrant pathway 712 includes a depolarization front marked by an arrowhead having positive charges on one side and negative charges on the other side. The positive charges represent depolarized tissue while the negative charges represent tissue at and/or near a rest potential and/or at a negative potential capable of depolarization. As mentioned in the Background section, such tissue may be referred to as the "excitable gap". As shown in FIG. 13, the depolarization front, and corresponding excitable gap, travel in a counter-clockwise direction. Further, while not explicitly shown, the depolarization front may trigger depolarization of tissue surrounding the re-entrant pathway 712 and hence cause depolarization of a substantial region of heart tissue. In general, a goal of antitachycardia pacing is to disrupt the re-entrant pathway and thereby eliminate any resultant undesirable depolarization of heart tissue.

An exemplary method for disrupting the re-entrant pathway includes delivering one or more stimulation pulses to one or more of the distal electrodes 720, 720' to stimulate a parasympathetic nerve and thereby cause release of acetylcholine in a region proximate to the re-entrant pathway 712. Further, after and/or during the delivery of such a pulse or pulses, antitachycardia pacing pulses are administered, for example, using the coil electrode 724 and at least one other electrode, e.g., ring, tip, can, etc. For example, after delivery of one or more stimulation pulses using the distal electrodes 720, 720' in a bipolar fashion, then a stimulation device delivers antitachycardia pacing pulses using one or more of the distal electrodes 720, 720' and the coil electrode 724 in a bipolar fashion (e.g., from distal electrodes 720, 720' to coil electrode 724).

Determining Vagal Tone and/or Inspiration/Postinspiration

Figure 15:
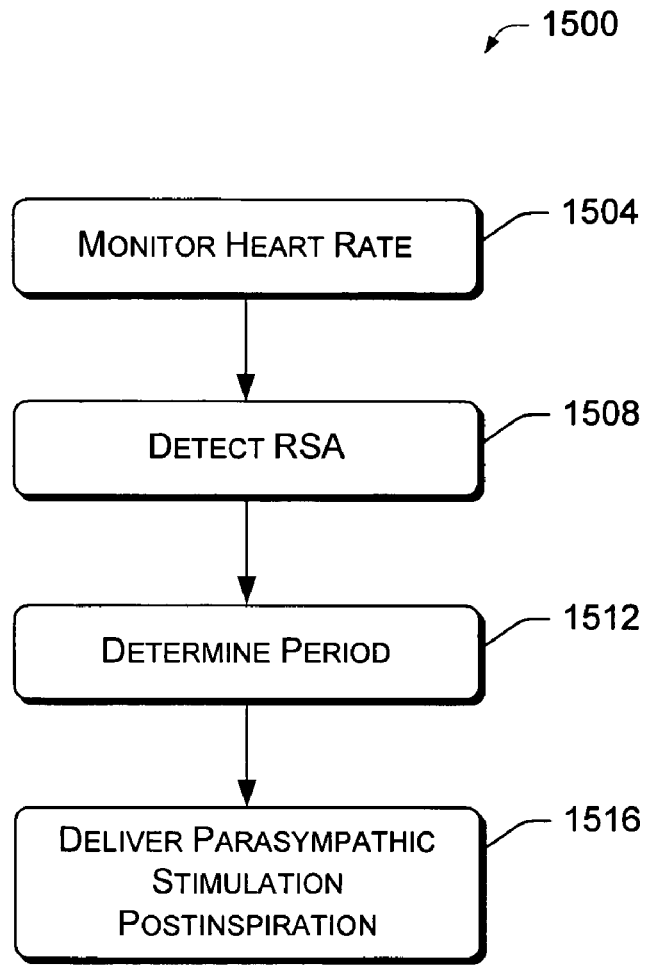
FIG. 15 is a block diagram of an exemplary method for delivering a stimulation pulse postinspiration.

As already mentioned, Mendelowitz noted that "cardiac vagal neurons recorded in vivo receive inhibitory synaptic input during inspiration, which is then followed by a rapid depolarization caused by excitatory synaptic input during postinspiration". Therefore, for a variety of reasons, the aforementioned exemplary methods and/or device optionally stimulate parasympathetic nerves postinspiration, i.e., not during inspiration. Referring to FIG. 15, an exemplary method 1500 for delivery of one or more nerve stimulation pulses postinspiration is shown. In a monitoring block 1504, a stimulation and/or other device monitors directly and/or indirectly heart rate. Next, in a detection block 1508, the stimulation and/or other device detects respiratory sinus arrhythmia. Following detection, in a determination block 1512, the stimulation and/or other device determines a period associated with inspiration. Next, in a delivery block 1516, the stimulation device delivers a stimulation pulse to a parasympathetic nerve. Also note that such a method can determine a patient's vagal tone.

In another exemplary method, a stimulation and/or other device monitors inspiration directly and/or indirectly through use of a ventilation module and/or sensor. In this exemplary method and the aforementioned method, parasympathetic stimulation pulse delivery during postinspiration only can decrease power demand on an implantable stimulation device. In yet another exemplary method, parasympathetic stimulation pulse delivery occurs during a refractory period to avoid stimulation of cardiac and/or other tissue. Of course, an exemplary combined method optionally includes delivery of a parasympathetic stimulation pulse postinspiration in a refractory period.

Selecting and/or Positioning Leads and/or Electrodes

An exemplary method for selecting and/or positioning a lead and/or an electrode is optionally implemented during implantation and/or after implantation. For example, during an implantation procedure, a patient is optionally instrumented to monitor heart function. For example, heart rate may be monitored via an EKG and contractility via arterial pressure sensors (e.g., the time derivative of the pressure can provide a good measure of contractility). In this example, monitoring of cardiac function and/or other functions may occur through use of external instrumentation and/or through use of implanted leads and/or sensors.

Consider a situation wherein parasympathetic tuning via parasympathetic nerve stimulation aims to decrease heart rate. In such a situation, an exemplary method includes adjusting pulse amplitude and/or pulse frequency to relatively high values, automatically or manually (e.g., an implantable device having a lead and/or electrode implantation, selection and/or positioning mode(s)). In this exemplary method, through use of stimulation pulses and monitoring of cardiac function and/or other functions, a lead and/or electrode is positioned during implantation to achieve an optimal and/or a satisfactory decrease in heart rate (e.g., an increase of therapeutic value). In this exemplary method, for example, a physician may slowly move a lead throughout an appropriate region and deliver pulses until a desired decrease in heart rate is seen maximally via monitoring.

In yet another exemplary method, a lead and/or an electrode are optionally positioned to decrease sympathetic activity while at the same time minimizing stimulation effects on heart rate. Once a "sweet spot" is found, then pulse parameters are optionally adjusted to minimize electrical power consumption, for example, by previously mentioned exemplary methods.

Conjunct to Sympathomimetics

Sympathomimetic drugs such as dobutamine and angiotensin II are known to increase heart rate and contractility (positive inotropic therapy), see, e.g., Levett et al., "Cardiac augmentation can be maintained by continuous exposure of intrinsic cardiac neurons to a beta-adrenergic agonist or angiotensin II," *J. Surg. Res.*, 66(2): 167–173 (1996). However, according to Burger et al., "Comparison of the occurrence of ventricular arrhythmias in patients with acutely decompensated congestive heart failure receiving dobutamine versus nesiritide therapy," *Am. J. Cardiol.*, 88(1): 35–39 (2001), ventricular arrhythmias, which are common in patients with congestive heart failure (CHF), may be exacerbated by positive inotropic therapy. Thus, various exemplary methods and/or stimulation devices presented herein may be implemented in conjunction with administration of inotropic agents. For example, stimulation of efferent parasympathetic nerves may release acetylcholine, which has an anti-arrhythmic effect, i.e., reduces the risk of arrhythmia.

Increasing Probability of Success

Figure 16:
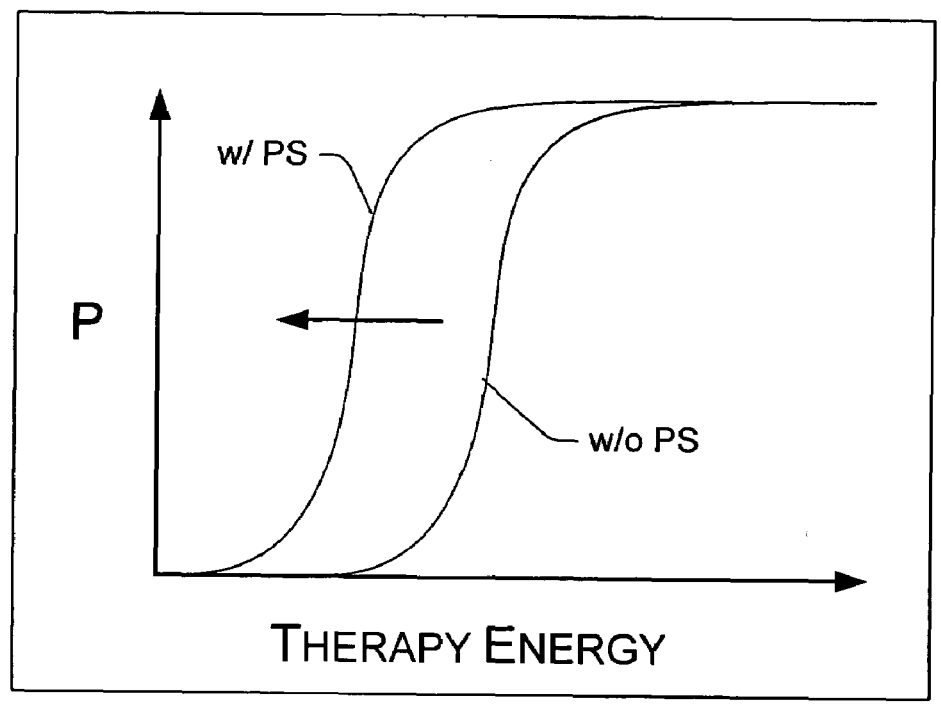
FIG. 16 is a graph having two plots of probability of success versus therapy energy, one with parasympathetic stimulation and the other without parasympathetic stimulation.

Various aforementioned exemplary methods and/or devices described herein are directed to increasing the probability of successful termination of ventricular tachyarrhythmias and/or decreasing the energy required to treat ventricular tachyarrhythmias. Referring to FIG. 16, a plot 1600 having two curves is shown for therapy energy versus probability of successful termination. One curve corresponds to probability of success without parasympathetic stimulation (w/o PS) while the other corresponds to probability of success with parasympathetic stimulation (w/PS). Note that the plot with parasympathetic stimulation is shifted to the left, therefore, indicating a greater probability of successful termination at a given therapy energy level. In general, the therapy energy in both plots corresponds to the energy required of antitachycardia pacing, cardioversion and/or defibrillation, etc. For example, various exemplary methods disclosed herein optionally allow for termination of ventricular tachyarrhythmia in a fewer number of pacing pulses and/or shocks. Further, stimulation of parasympathetic nerves before, during and/or after antitachycardia pacing, cardioversion and/or defibrillation generally helps to prevent reinitiation of ventricular tachyarrhythmia.

An exemplary method for increasing probability of successful termination of ventricular tachyarrhythmias or decreasing the energy required to treat ventricular tachyarrhythmias includes delivering a stimulation pulse to a lead having one or more electrodes positioned proximate to a parasympathetic pathway after detecting a ventricular tachyarrhythmia. Further, according to such an exemplary method, a determination as to whether to deliver parasympathetic stimulation may be made. For example, depending on history of parasympathetic stimulation, probability that parasympathetic stimulation may help decrease risk of reinitiation of an arrhythmia, etc., an exemplary method may determine that parasympathetic stimulation is not warranted and thus delivery an appropriate therapy at a first energy level. However, if such a method determines that parasympathetic stimulation is warranted, then the appropriate therapy may be delivered at a second energy level wherein the second energy level is less than the first energy level. In such instances, energy level may correspond to amplitude and/or duty. The appropriate therapy is generally selected from antitachycardia pacing therapy, cardioversion therapy and/or defibrillation therapy.

Where a tiered therapy is implemented, an exemplary stimulation device may include a table relating parasympathetic stimulation with various tiers of appropriate therapy (e.g., antitachycardia pacing therapy, cardioversion therapy and/or defibrillation therapy). For example, consider Table 1 below:

TABLE 1

Tier of Therapy, Type of Arrhythmia and Probability of Success.

| | A1 | A1 | A1 | A2 | A2 | A2 |
|---|---|---|---|---|---|---|
| PS | w/PS | w/o PS | w/PS | w/PS | w/o PS | w/PS |
| Tier-E | E1 | E1 | E2 | E1 | E1 | E2 |
| Tier 1 | 65% | 30% | 50% | 25% | 5% | 15% |
| Tier 2 | 75% | 50% | 65% | 35% | 25% | 30% |
| Tier 3 | 95% | 60% | 75% | 85% | 60% | 75% |

According to Table 1, an exemplary device includes probability data given as percent chance of termination of a certain type of arrhythmia (e.g., A1, A2, etc.) with parasympathetic stimulation at first and second energy levels (E1, E2, etc.) and without parasympathetic stimulation at the first energy level. The probabilities are given with respect to a particular tier of therapy (e.g., Tier 1, Tier 2, Tier 3, etc.) administered at a given energy level. The data in Table 1 indicate that parasympathetic stimulation increases probability of success. In such instances, a determination may be made as to whether to deliver parasympathetic stimulation. If a determination is made to deliver parasympathetic stimulation, then a lesser tier energy level may be used to achieve a result that is better than without parasympathetic stimulation at a higher tier energy level.

CONCLUSION

Although exemplary methods and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and/or devices.

Figure 17:
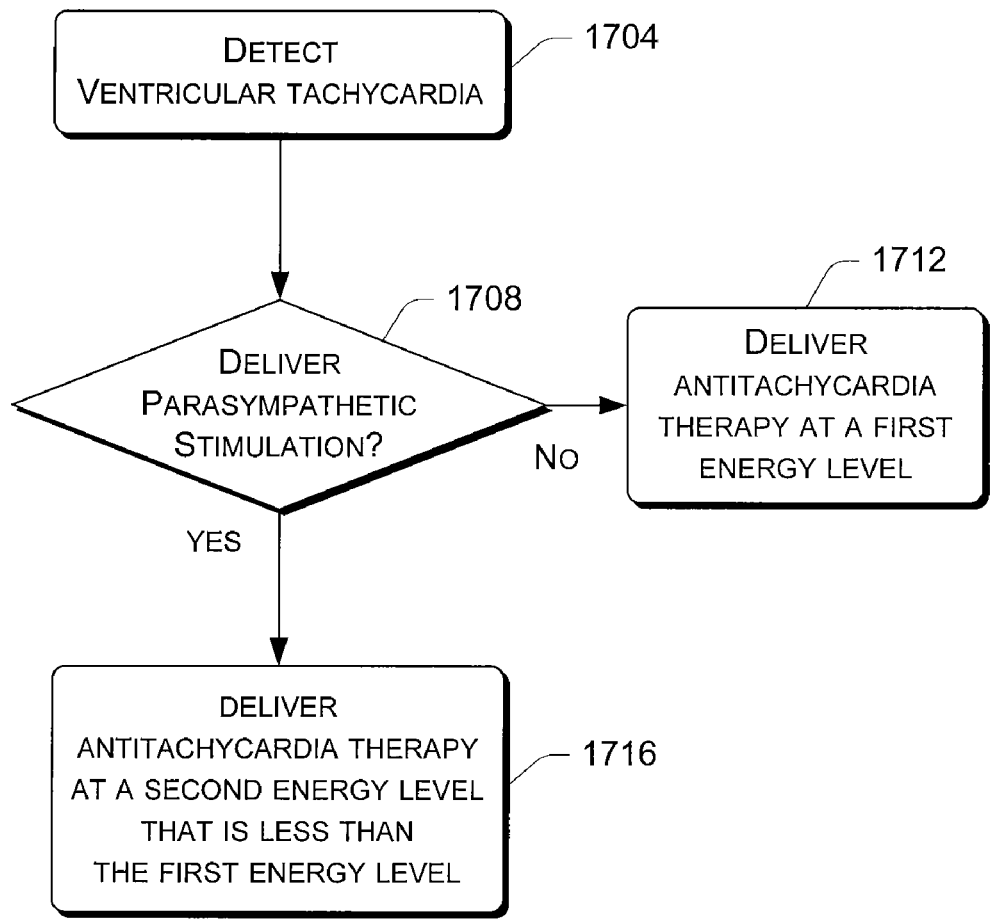
FIG. 17 is a block diagram of an exemplary method for delivering antitachycardia therapy.

FIG. 17 shows a block diagram of an exemplary method for delivering antitachycardia therapy 1700. In a detection block 1704, the method 1700 includes detecting a ventricular tachyarrhythmia. A decision block 1708 determines whether to deliver parasympathetic stimulation to a lead having one or more electrodes positioned proximate to a parasympathetic pathway. If the decision block 1708 decides not to call for parasympathetic stimulation, then the method 1700 enters a delivery block 1712 that delivers antitachycardia therapy at a first energy level. However, if the decision block 1708 decides to call for parasympathetic stimulation, then the method 1700 enters a delivery block 1716 that delivers antitachycardia therapy at antitachycardia therapy at a second energy level where the second energy level is less than the first energy level. For example, the plot 1600 of FIG. 16 shows that delivery of parasympathetic stimulation allows for use of a lower energy antitachycardia therapy (e.g., antitachycardia pacing, cardioversion and/or defibrillation, etc.).

What is claimed is:

1. A method comprising:
    detecting a ventricular tachyarrhythmia;
    determining whether to deliver parasympathetic stimulation to a lead having one or more electrodes positioned proximate to a parasympathetic pathway;
    if the determining does not call for parasympathetic stimulation, then delivering antitachycardia therapy at a first energy level; and,
    if the determining calls for parasympathetic stimulation, then delivering antitachycardia therapy at second energy level wherein the second energy level is less than the first energy level.

2. The method of claim 1 wherein delivering antitachycardia therapy comprises delivering cardioversion therapy.

3. The method of claim 1 wherein delivering antitachycardia therapy comprises delivering defibrillation therapy.

* * * * *